(12) United States Patent
Jalce et al.

(10) Patent No.: US 10,071,080 B2
(45) Date of Patent: *Sep. 11, 2018

(54) MIF INHIBITORS FOR THE ACUTE OR CHRONIC TREATMENT OF PULMONARY HYPERTENSION

(71) Applicants: MIFCARE, Paris (FR); INSERM (INSTITUT NATIONAL DE LA SANTÉ ET DE LA RECHERCHE MÉDICALE), Paris (FR); UNIVERSITÉ PARIS-SUD 11, Orsay (FR)

(72) Inventors: Gaël Jalce, Saint-Michel-sur-Orge (FR); Christophe Guignabert, Arceuil (FR); Morane Le Hiress, Maisons-Alfort (FR); Ly Tu, Ivry-sur-Seine (FR); Bernardin Akagah, Massy (FR)

(73) Assignees: MIFCARE, Paris (FR); INSERM (INSTITUT NATIONAL DE LA SANTÉ ET DE LA RECHERCHE MÉDICALE), Paris (FR); UNIVERSITÉ PARIS-SUD 11, Orsay (FR)

(*) Notice: Subject to any disclaimer, the term of this patent is extended or adjusted under 35 U.S.C. 154(b) by 1 day.

This patent is subject to a terminal disclaimer.

(21) Appl. No.: 15/311,649

(22) PCT Filed: May 18, 2015

(86) PCT No.: PCT/EP2015/060914
§ 371 (c)(1),
(2) Date: Nov. 16, 2016

(87) PCT Pub. No.: WO2015/173433
PCT Pub. Date: Nov. 19, 2015

(65) Prior Publication Data
US 2017/0079958 A1  Mar. 23, 2017

(30) Foreign Application Priority Data
May 16, 2014 (EP) .................................... 14168742

(51) Int. Cl.
*A61K 31/423* (2006.01)
*C07D 263/58* (2006.01)
*C07D 413/06* (2006.01)
*C07D 235/28* (2006.01)

(52) U.S. Cl.
CPC .................................. *A61K 31/423* (2013.01)

(58) Field of Classification Search
None
See application file for complete search history.

(56) References Cited

U.S. PATENT DOCUMENTS
2013/0004506 A1  1/2013  Miller et al.

FOREIGN PATENT DOCUMENTS
WO  01/05770 A1  1/2001
WO  2010/021693 A2  2/2010

OTHER PUBLICATIONS

Zhang, et al., Molecular Medicine, 18:215. (Year: 2012).*
Aliev, et al., Agrokhimiya, 9:118 (Abstract only) (Year: 1991).*
STN/CAPLUS RN 354793-13-8. (Year: 2001).*
STN/CAPLUS RN 286008-69-3. (Year: 2000).*
U.S. Appl. No. 15/302,648, filed Oct. 2016, Jalce, G., et al.*
STN/CAPLUS RN 13982273-83-4. (Year: 2012).*
Yamato et al., "Synthesis of 3-substituted benzoxazoline-2-thiones", Chemical and Pharmaceutical Bulletin, Jan. 1, 1983, pp. 1733-1737, vol. 31, No. 5.

* cited by examiner

*Primary Examiner* — Michael P Barker
(74) *Attorney, Agent, or Firm* — Whitham & Cook, P.C.

(57) ABSTRACT

The present invention relates to the use of compounds of general Formula I and pharmaceutically acceptable enantiomers, salts or solvates thereof, for treating pulmonary hypertension in a subject.

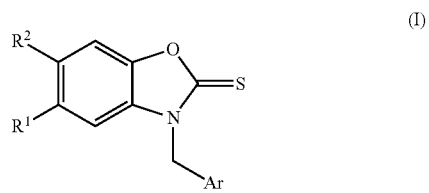

(I)

19 Claims, 6 Drawing Sheets

MIF INHIBITORS FOR THE ACUTE OR CHRONIC TREATMENT OF PULMONARY HYPERTENSION

The invention was made under a joint research agreement which includes the following parties: MIFCARE, INSERM (INSTITUT NATIONAL DE LA SANTE ET DE LA RECHERCHE MEDICALE), and UNIVERSITE PARIS-SUD 11.

FIELD OF INVENTION

The present invention relates to the treatment of pulmonary hypertension (PH). In particular, the present invention relates to the use of compound of general Formula I:

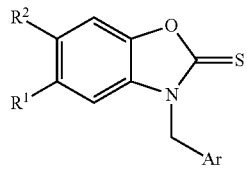

wherein R1, R2 and Ar are as defined below, for treating pulmonary hypertension.

BACKGROUND OF INVENTION

Vascular remodeling and perivascular infiltration, occurring mostly in the small to mid-sized pulmonary arterioles (<500 µm), are critical events of most forms of pulmonary hypertension (PH) and frequently leads to progressive functional decline in patients despite treatment with currently available therapies. Although the exact mechanisms leading to the onset and progression of PH are still largely unclear, a complex interplay between pulmonary endothelial dysfunction and inflammation is strongly suspected to influence the development of the disease (Huertas et al, Circulation, 2014, 129: 1332-1340).

Prostacyclin analogs such as Epoprostenol are indicated in PH treatment. However it is administered via continuous infusion that requires a semi-permanent central venous catheter. This delivery system can cause sepsis and thrombosis. Moreover, prostacyclin analogs are unstable, their half-life is of 3 to 5 minutes and the infusion has to be continuous since interruption can be fatal. Due to the lack of tolerability, the skilled artisan tends to treat PH with endothelin receptor antagonists (ERAs) as described in patent application US2004/102361 or phosphodiesterase type 5 (PDE5) inhibitors as described in patent application WO2009/115235.

Most of these drugs constitute palliative care and cannot cure PH. Indeed these drugs taken separately only have a limited action and act mainly on the balance between vasoconstriction and vasodilatation that constituted only one component of this complex and multifactorial disease.

Thus, there is a need to discover and/or develop new, better-tolerated and more powerful therapeutic small molecules for treating PH. In addition, compounds able to control different causal-mechanisms deregulated in PH (for example, the excessive proliferation/survival of pulmonary vascular cells and/or the abnormal inflammation/autoimmunity) would be a major step forward curing PH.

The present invention demonstrates that compounds having the Formula I:

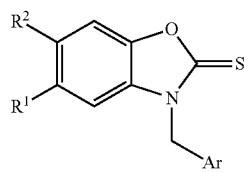

(wherein Ar, $R^1$ and $R^2$ are as defined below) are effective to treat PH at a low concentration in a rat model of PH due to their action on both lung inflammation and pulmonary vascular cell proliferation/survival.

SUMMARY

The present invention thus relates to a compound of Formula I and pharmaceutically acceptable enantiomers, salts or solvates thereof, for use in the treatment of pulmonary hypertension in a subject in need thereof, wherein said compound of Formula I is:

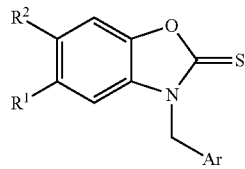

wherein:
Ar represents aryl or heteroaryl group, preferably selected from phenyl, pyridine, indole, indazole, 7-azaindole, quinoline, quinolinone, dihydroquinolinone, dihydroquinaolinone, imidazole, pyrrole, or pyrazol, benzimidazolone, benzoxazolone, benzimidazole-thione, benzotriazole, benimidazole, benzoxazinone, indolinedione, hydroxypyridinone, benzothiazolamine; optionally substituted by or more substituents selected from halo, hydroxyl, nitro, amino, amido, carbamate, carbamide, sulfonamide, alkoxy, alkyl, haloalkyl, alkenyl, alkynyl, aryl, heteroaryl, 4-amino-cyclobut-3-ene-1,2-dione, 3-hydroxythiophen-2-yl-metanone; preferably Ar represents an optionally substituted phenyl group;
$R^1$-$R^2$ are the same or different and represent a hydrogen atom or a group selected from hydroxyl, amino, halo, nitro, cyano, carboxylic acid, alkyl, cycloalkyl, alkenyl, alkynyl, aryl, heteroaryl, hydroxyalkyl, alkoxy, C1-C8 acyl, haloalkyl, preferably $R^1$-$R^2$ represent hydrogen, alkyl, cycloalkyl or haloalkyl, more preferably hydrogen, methyl or $CF_3$.

In one embodiment, the compound of Formula I of the invention has the Formula Ia:

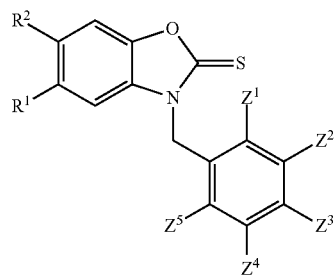

and pharmaceutically acceptable enantiomers, salts or solvates thereof, wherein:
- $R^1$-$R^2$ are the same or different and represent a hydrogen atom or a group selected from hydroxyl, amino, halo, nitro, cyano, carboxylic acid, alkyl, cycloalkyl, alkenyl, alkynyl, aryl, heteroaryl, hydroxyalkyl, alkoxy, C1-C8 acyl, haloalkyl, preferably $R^1$-$R^2$ represent hydrogen, alkyl, cycloalkyl or haloalkyl, more preferably hydrogen, methyl or $CF_3$;
- $Z^1$ represents a hydrogen atom or a group selected from halo, hydroxyl, nitro, amino, amido, carbamate, carbamide, sulfonamide, alkoxy, alkyl, haloalkyl, alkenyl, alkynyl, aryl, heteroaryl, 4-amino-cyclobut-3-ene-1,2-dione, 3-hydroxythiophen-2-yl-metanone, or form with $Z^2$ an aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; preferably $Z^1$ represents H, F, Cl, Br, $NO_2$, $NH_2$, $NMe_2$, OH, OMe, $CH_3$ or $CF_3$;
- $Z^2$ represents a hydrogen atom or a group selected from halo, hydroxyl, nitro, amino, amido, carbamate, carbamide, sulfonamide, alkoxy, alkyl, haloalkyl, alkenyl, alkynyl, aryl, heteroaryl, 4-amino-cyclobut-3-ene-1,2-dione, 3-hydroxythiophen-2-yl-metanone, or form with $Z^1$ or $Z^3$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; preferably $Z^2$ represents H, F, Cl, Br, $NO_2$, $NH_2$, $NMe_2$, OH, OMe, $CH_3$ or $CF_3$;
- $Z^3$ represents a hydrogen atom or a group selected from halo, hydroxyl, nitro, amino, amido, carbamate, carbamide, sulfonamide, alkoxy, alkyl, haloalkyl, alkenyl, alkynyl, aryl, heteroaryl, 4-amino-cyclobut-3-ene-1,2-dione, 3-hydroxythiophen-2-yl-metanone, or form with $Z^2$ or $Z^4$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; preferably $Z^3$ represents H, F, Cl, Br, $NO_2$, $NH_2$, $NMe_2$, OH, OMe, $CH_3$ or $CF_3$;
- $Z^4$ represents a hydrogen atom or a group selected from halo, hydroxyl, nitro, amino, amido, carbamate, carbamide, sulfonamide, alkoxy, alkyl, haloalkyl, alkenyl, alkynyl, aryl, heteroaryl, 4-amino-cyclobut-3-ene-1,2-dione, 3-hydroxythiophen-2-yl-metanone, or form with $Z^3$ or $Z^5$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; preferably $Z^4$ represents H, F, Cl, Br, $NO_2$, $NH_2$, $NMe_2$, OH, OMe, $CH_3$ or $CF_3$;
- $Z^5$ represents a hydrogen atom or a group selected from halo, hydroxyl, nitro, amino, amido, carbamate, carbamide, sulfonamide, alkoxy, alkyl, haloalkyl, alkenyl, alkynyl, aryl, heteroaryl, 4-amino-cyclobut-3-ene-1,2-dione, 3-hydroxythiophen-2-yl-metanone, or form with $Z^4$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; preferably $Z^5$ represents H, F, Cl, Br, $NO_2$, $NH_2$, $NMe_2$, OH, OMe, $CH_3$ or $CF_3$.

In one embodiment, the compound of Formula I of the invention has Formula Ib:

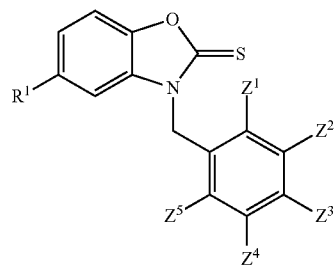

and pharmaceutically acceptable enantiomers, salts or solvates thereof, wherein $R^1$, $Z^1$, $Z^2$, $Z^3$, $Z^4$ and $Z^5$ are as defined above.

In one embodiment, the compound of Formula I is one of the following:
3-(3-hydroxybenzyl)-5-methylbenzo[d]oxazole-2(3H)-thione,
3-(2-methoxybenzyl)-5-methylbenzo[d]oxazole-2(3H)-thione,
3-benzyl-5-methylbenzo[d]oxazole-2(3H)-thione,
3-(4-fluoro-3-hydroxybenzyl)benzo[d]oxazole-2(3H)-thione,
3-(4-fluoro-3-hydroxybenzyl)-5-(trifluoromethyl)benzo[d]oxazole-2(3H)-thione.

In one embodiment, the compound of Formula I of the invention has the following formula:

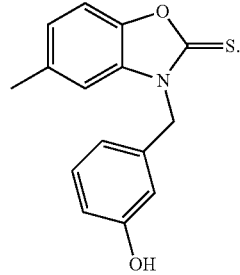 [SMILES: Cc1ccc2oc(=S)n(Cc3cccc(O)c3)c2c1]

In another embodiment, the compound of Formula I of the invention has the following formula:

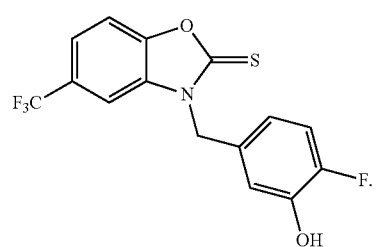 [SMILES: Oc1cc(Cn2c(=S)oc3ccc(C(F)(F)F)cc32)ccc1F]

The present invention also relates to a pharmaceutical composition for use in the treatment of pulmonary hypertension comprising the compound as described hereinabove and pharmaceutically acceptable excipients.

The present invention also relates to a medicament for use in the treatment of pulmonary hypertension comprising the compound as described hereinabove.

In one embodiment, the subject is diagnosed with pulmonary hypertension. In another embodiment, the subject is at risk of developing pulmonary hypertension. In one embodiment, said subject is an adult, a teenager, a child, a young child or a new born child.

In one embodiment, the compound, pharmaceutical composition or medicament of the invention is to be administered to a subject in need thereof by topical, subcutaneous, oral, transdermal, nasal, parenteral, intratracheal administration.

In one embodiment, the compound of the invention is for the acute treatment of pulmonary hypertension. In another embodiment, the compound of the invention is for the chronic treatment of pulmonary hypertension.

In one embodiment, pulmonary hypertension is selected from Groups 1, 1', 1", 2, 3, 4 and 5. In one embodiment, pulmonary hypertension is pulmonary arterial hypertension. In one embodiment, pulmonary arterial hypertension is selected from the group comprising idiopathic PAH, heritable PAH, drug- and toxin-induced PAH, PAH associated with connective tissue diseases, PAH complication of HIV infection, portal hypertension; congenital heart diseases (CHD); schistosomiasis.

DEFINITIONS

In the present invention, the following terms have the following meanings:

"Treatment", "treat" and "treating" refers to therapeutic treatment, prophylactic or preventative measures and deferment of the disease onset; wherein the object is to delay, prevent or slow down (lessen) the targeted pathologic condition or disorder. Those in need of treatment include those already with pulmonary hypertension, as well as those prone to have pulmonary hypertension, or those in whom pulmonary hypertension is to be prevented or delayed. In one embodiment, a subject is successfully "treated" for pulmonary hypertension if, after receiving a therapeutic amount of the compound according to the invention, the subject shows amelioration in the patient's World Health Organization (WHO) functional class and/or a measurable decrease in pulmonary vascular resistance (PVR), and/or improvement in quality of life issues. The above parameters for assessing successful treatment and improvement in the disease are readily measurable by routine procedures familiar to the skilled artisan.

"WHO" refers to the WHO functional classification system that recognizes the importance of near syncope and syncope in the symptom complex of patients with PH. Syncope is generally thought to carry a grave prognosis in patients with PH. For this reason, PH patients who have experienced a syncopal episode are generally assigned to WHO functional class IV (although this is not explicitly stated in the WHO functional classification system).

WHO Classification of functional status of patients with PH is shown in the table below:

| Class | Description |
|---|---|
| I | Patients with PH in whom there is no limitation of usual physical activity; ordinary physical activity does not cause increased dyspnea, fatigue, chest pain or pre-syncope. |
| II | Patients with PH who have mild limitation of physical activity. There is no discomfort at rest, but normal physical activity causes increased dyspnea, fatigue, chest pain or pre-syncope. |
| III | Patients with PH who have a marked limitation of physical activity. There is no discomfort at rest, but less than ordinary activity causes increased dyspnea, fatigue, chest pain or pre-syncope. |
| IV | Patients with PH who are unable to perform any physical activity and who may have signs of right ventricular failure at rest. Dyspnea and/or fatigue may be present at rest and symptoms are increased by almost any physical activity. |

"Pulmonary vascular resistance (PVR)" refers to the resistance offered by the vasculature of the lungs as described in Galiè et al. (2004 Eur Heart J 25: 2243-2278). The decrease in PVR is a key parameter for the classification which takes into account several parameters. PVR is measured as follows:

PVR=(mean pulmonary arterial pressure (mPAP mmHg)−pulmonary capillary wedge pressure medium blocked (or PCAPm mmHg)×80)/cardiac output (L/min).

In one embodiment, if the PVR value is greater than 300 dynes·cm$^{-5}$, there is evidence of PH.

"Chronic treatment" may first refer to the treatment of a condition or disease that is persistent or otherwise long-lasting in its effects. The term "chronic" is usually applied when the course of the disease lasts for more than one month, preferably more than three months. In another embodiment, the term "chronic treatment" refers to the continuous treatment of a subject for at least 1 month, preferably at least 3 months, more preferably at least 1 year, or as long as the subject will need it (such as, for example, if any timeout of the treatment leads to the reappearance of the symptoms of the disease).

"Acute treatment" may first refer to the treatment of a condition or disease with a rapid onset and/or a short course of a said condition or disease. In another embodiment, the term "acute treatment", by opposition to a chronic treatment, refers to a treatment limited in time, such as, for example, for less than 1 year, less than 6 months, less than 1 month or less than 2 weeks. According to this embodiment, the disease is cured by the acute treatment, and the discontinuation of the treatment does not lead to the reappearance of the symptoms of the disease.

"Pharmaceutically acceptable" means that the ingredients of a pharmaceutically composition are compatible with each other and not deleterious to the subject.

"Pharmaceutically acceptable excipient" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, and general safety and purity standards as required by FDA Office of Biologics standards.

"Therapeutically effective amount" refers to the level or amount of agent that is aimed at, without causing significant negative or adverse side effects to the target, delaying or preventing the onset of pulmonary hypertension; slowing down or stopping the progression, aggravation, or deterioration of one or more symptoms of pulmonary hypertension; bringing about ameliorations of the symptoms of pulmonary hypertension; reducing the severity or incidence of pulmonary hypertension; or curing pulmonary hypertension. An effective amount may be administered prior to the onset of pulmonary hypertension, for a delayed, prophylactic or preventive action. Alternatively or additionally, the effective amount may be administered after initiation of pulmonary hypertension, for a therapeutic action.

"Subject" refers to a mammal, preferably a human. In one embodiment, a subject may be a patient, i.e. a person receiving medical attention, undergoing or having underwent a medical treatment, or monitored for the development of a disease.

"About": preceding a figure means plus or less 10% of the value of said figure.

The term "MIF" refers to macrophage migration inhibitory factor or active fragment thereof. An active fragment of MIF may comprise a fragment of a portion of the MIF protein harboring the tautomerase enzymatic activity, or a fragment that is capable of binding to one of its receptors.

"Inhibitor of MIF" refers to any agent that attenuates, inhibits, opposes, counteracts, or decreases the biological activity of MIF. A MIF antagonist may be an agent that inhibits or neutralizes MIF biological function (including, without limitation, small molecules, recombinant peptides/proteins and anti-MIF antibodies); an agent that prevents the binding of MIF to one of its receptor such as CD74, and/or CD44 and/or CXCRs (including, without limitation, an anti-CD74 antibody or an anti-MIF antibody or a fragment thereof). In one embodiment, the inhibitor of MIF is an inhibitor of MIF CD74 axis, preferably an inhibitor of MIF CD74 pathway, wherein the term MIF CD74 pathway refers to a multi-step biochemical pathway. Each step in this pathway, as in many biochemical pathways, not only passes information downstream but also receives feedback from messengers produced later in the pathway to either enhance or suppress earlier steps in the pathway. According to a specific embodiment, the inhibitor of MIF of the invention inhibits MIF binding to CD74 and/or CXCRs (including CXCR2, CXCR4 and/or CXCR7).

"biological function of MIF" refers to the ability of MIF to carry out one or more of the biological functions of MIF including, but not limited to, sustaining pulmonary vascular cell survival and/or proliferation, promoting endothelial pro-inflammatory phenotype, cytokine production and release, modulating cell metabolism, binding to CD74, activating mitogen activated protein kinase (MAPK) and Src signaling pathways (e.g., ERK1/2, JNK, PI3K, and SAPK MAPK signaling), inhibiting p53, acting as a tautomerase, and/or acting as a thiol reductase.

"alkyl" by itself or as part of another substituent refers to a hydrocarbyl radical of Formula $C_nH_{2n+1}$, wherein n is a number greater than or equal to 1. Generally, alkyl groups of this invention comprise from 1 to 6 carbon atoms. Alkyl groups may be linear or branched and may be substituted as indicated herein. Examples of alkyl groups are methyl, ethyl, n-propyl, i-propyl, butyl and its isomers (e.g. n-butyl, i-butyl and t-butyl); pentyl and its isomers, hexyl and its isomers.

"alkenyl" refers to unsaturated hydrocarbyl group, which may be linear or branched, comprising one or more carbon-carbon double bonds. Suitable alkenyl groups comprise between 2 and 6 carbon atoms, preferably between 2 and 4 carbon atoms, still more preferably between 2 and 3 carbon atoms. Examples of alkenyl groups are ethenyl, 2-propenyl, 2-butenyl, 3-butenyl, 2-pentenyl and its isomers, 2-hexenyl and its isomers, 2,4-pentadienyl and the like.

"alkynyl" refers to a class of monovalent unsaturated hydrocarbyl groups, wherein the unsaturation arises from the presence of one or more carbon-carbon triple bonds. Alkynyl groups typically, and preferably, have the same number of carbon atoms as described above in relation to alkenyl groups. Non limiting examples of alkynyl groups are ethynyl, 2-propynyl, 2-butynyl, 3-butynyl, 2-pentynyl and its isomers, 2-hexynyl and its isomers- and the like.

"alkoxy" refers to any O-alkyl group.

"alkylthio" refers to any S-alkyl group.

"aryl" refers to a polyunsaturated, aromatic hydrocarbyl group having a single ring (i.e. phenyl) or multiple aromatic rings fused together (e.g. naphtyl) or linked covalently, typically containing 5 to 12 atoms; preferably 6 to 10, wherein at least one ring is aromatic. The aromatic ring may optionally include one to two additional rings (either cycloalkyl, heterocyclyl or heteroaryl) fused thereto. Aryl is also intended to include the partially hydrogenated derivatives of the carbocyclic systems enumerated herein. Non-limiting examples of aryl comprise phenyl, biphenylyl, biphenylenyl, 5- or 6-tetralinyl, naphthalen-1- or -2-yl, 4-, 5-, 6 or 7-indenyl, 1-2-, 3-, 4- or 5-acenaphtylenyl, 3-, 4- or 5-acenaphtenyl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl.

"heteroaryl" as used herein by itself or as part of another group refers but is not limited to 5 to 12 carbon-atom aromatic rings or ring systems containing 1 to 2 rings which are fused together or linked covalently, typically containing 5 to 6 atoms; at least one of which is aromatic in which one or more carbon atoms in one or more of these rings can be replaced by oxygen, nitrogen or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1(6H)-yl, 2-oxopyridin-1 (2H)-yl, 6-oxo-pyrudazin-1(6H)-yl, 2-oxopyridin-1(2H)-yl, 1,3-benzodioxolyl, quinolinyl, isoquinolinyl, cinnolinyl, quinazolinyl, quinoxalinyl.

"alkylaryl" refers to any group alkyl-aryl-.

"alkylheteroaryl" refers to any group alkyl-heteroaryl-.

"halo" refers to fluoro, chloro, bromo, iodo.

"haloalkyl" refers to any group alkyl group substituted by one or more halo group. Examples of preferred haloalkyl groups are $CF_3$, $CHF_2$ and $CH_2F$.

"hydroxyalkyl" refers to any alkyl group substituted by at least one hydroxyl group.

"cycloalkyl" as used herein is a cyclic alkyl group, that is to say, a monovalent, saturated, or unsaturated hydrocarbyl group having 1 or 2 cyclic structures. Cycloalkyl includes monocyclic or bicyclic hydrocarbyl groups. Cycloalkyl groups may comprise 3 or more carbon atoms in the ring and generally, according to this invention comprise from 3 to 10, more preferably from 3 to 8 carbon atoms still more preferably from 3 to 6 carbon atoms. Examples of cycloalkyl groups include but are not limited to cyclopropyl, cyclobutyl, cyclopentyl, cyclohexyl.

"heterocyclyl" or "heterocycle" as used herein by itself or as part of another group refer to non-aromatic, fully saturated or partially unsaturated cyclic groups (for example, 3 to 7 member monocyclic, 7 to 11 member bicyclic, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen, oxygen and/or sulfur atoms, where the nitrogen and sulfur heteroatoms may optionally be oxidized and the nitrogen heteroatoms may optionally be quaternized. Any of the carbon atoms of the heterocyclic group may be substituted by oxo (for example piperidone, pyrrolidinone). The heterocyclic group may be attached at any heteroatom or carbon atom of the ring or ring system, where valence allows. The rings of multi-ring heterocycles may be fused, bridged and/or joined through one or more spiro atoms. Non limiting exemplary heterocyclic groups include oxetanyl, piperidinyl, azetidinyl, 2-imidazolinyl, pyrazolidinyl imidazolidinyl, isoxazolinyl, oxazolidinyl, isoxazolidinyl, thiazolidinyl, isothiazolidinyl, piperidinyl, 3H-indolyl, indolinyl, isoindolinyl, 2-oxopiperazinyl, piperazinyl, homopiperazinyl, 2-pyrazolinyl, 3-pyrazolinyl, tetrahydro-2H-pyranyl, 2H-pyranyl, 4H-pyranyl, 3,4-dihydro-2H-pyranyl, 3-dioxolanyl, 1,4-dioxanyl, 2,5-dioximidazolinyl, 2-oxopiperidinyl, 2-oxopyrrolodinyl, indolinyl, tetrahydropyranyl, tetrahydrofuranyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, thiomorpholin-4-ylsulfoxide, thiomorpholin-4-ylsulfone, 1,3-dioxolanyl, 1,4-oxathianyl, 1H-pyrrolizinyl, tetrahydro-1,1-dioxothiophenyl, N-formylpiperazinyl, and morpholin-4-yl.

"amino" refers to any compound derived from ammoniac $NH_3$ by substitution of one or more hydrogen atoms with an organic radical. Amino preferably refers to —$NH_2$, —NHR and —NRR' wherein R and R are preferably alkyl groups. Therefore "amino includes monoalkylamino and dialkylamino groups.

"amide" refers to a group —CO—NH—R or —NH—CO—R wherein R represents preferably an alkyl group, as defined above.

"aminoacid" refers to a group —O—CO—CHR—$NH_2$ or —NH—CHR—CO—OH wherein R represent the lateral chain of the aminoacid, preferably the lateral chain of a natural aminoacid.

"carbamate" refers to a group —O—CO—NRR' or —NR—CO—OR' wherein R and R' represent preferably each independently alkyl groups.

"carbamide" refers to a group —NR—CO—NR'R" wherein R, R' and R" represent preferably each independently alkyl groups.

"carbonate" refers to a group —O—CO—OR wherein R represents preferably an alkyl group.

"ester" refers to a group —O—CO—R or —CO—OR wherein R represents preferably an alkyl group.

"thioester" refers to a group —S—CO—R or —CO—SR wherein R represents preferably an alkyl group.

"phosphonate" refers to a group —O—PO(OR)$_2$ wherein R represents H, alkyl, Na or Ca.

"phosphonate methyloxy" refers to a group —O—$CH_2$—O—PO(OR)$_2$ wherein R represents H, alkyl, Na or Ca.

"phosphonate methylamino" refers to a group —NH—$CH_2$—O—PO(OR)$_2$ wherein R represents H, alkyl, Na or Ca.

"sulfonamide" refers to a group —$SO_2$—NRR' or —NR—$SO_2$—R' wherein R and R' represent preferably each independently alkyl groups.

"solvate" is used herein to describe a molecular complex comprising the compound of the invention and one or more pharmaceutically acceptable solvent molecules, for example, ethanol.

DETAILED DESCRIPTION

The present invention relates to a compound of general Formula I, and pharmaceutically acceptable enantiomers, salts or solvates thereof, for treating, or for use in the treatment of pulmonary hypertension (PH), wherein said compound of general Formula I is as follows:

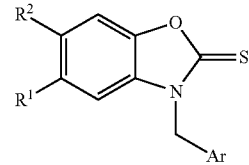

wherein:
Ar represents aryl or heteroaryl group, preferably selected from phenyl, pyridine, indole, indazole, 7-azaindole, quinoline, quinolinone, dihydroquinolinone, dihydroquinaolinone, imidazole, pyrrole, or pyrazol, benzimidazolone, benzoxazolone, benzimidazole-thione, benzotriazole, benimidazole, benzoxazinone, indolinedione, hydroxypyridinone, benzothiazolamine; optionally substituted by or more substituents selected from halo, hydroxyl, hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, 3-hydroxythiophen-2-yl-metanone; preferably optionally substituted by or more substituents selected from halo, hydroxyl, nitro, amino, amido, carbamate, carbamide, sulfonamide, alkoxy, alkyl, haloalkyl, alkenyl, alkynyl, aryl, heteroaryl, 4-amino-cyclobut-3-ene-1,2-dione, 3-hydroxythiophen-2-yl-metanone; preferably Ar represents an optionally substituted phenyl group;

$R^1$-$R^2$ are the same or different and represent a hydrogen atom or a group selected from hydroxyl, amino, halo, nitro, cyano, carboxylic acid, alkyl, cycloalkyl, alkenyl, alkynyl, aryl, heteroaryl, hydroxyalkyl, alkoxy, C1-C8 acyl, haloalkyl, preferably $R^1$-$R^2$ represent hydrogen, alkyl, cycloalkyl or haloalkyl, more preferably hydrogen, methyl or $CF_3$.

According to one embodiment, the invention relates to a compound of general Formula I', and pharmaceutically acceptable enantiomers, salts or solvates thereof, for treating, or for use in the treatment of pulmonary hypertension (PH), wherein said compound of general Formula I is as follows:

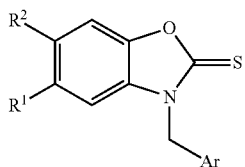

wherein:
Ar represents aryl or heteroaryl group, preferably selected from phenyl, pyridine, indole, indazole, 7-azaindole, quinoline, quinolinone, dihydroquinolinone, dihydroquinaolinone, imidazole, pyrrole, or pyrazol, benzimidazolone, benzoxazolone, benzimidazole-thione, benzotriazole, benimidazole, benzoxazinone, indolinedione, hydroxypyridinone, benzothiazolamine; optionally substituted by or more substituents selected from halo, hydroxyl, nitro, amino, amido, carbamate, carbamide, sulfonamide, alkoxy, alkyl, haloalkyl, alkenyl, alkynyl, aryl, heteroaryl, 4-amino-cyclobut-3-ene-1,2-dione, 3-hydroxythiophen-2-yl-metanone; preferably Ar represents an optionally substituted phenyl group;

$R^1$-$R^2$ are the same or different and represent a hydrogen atom or a group selected from hydroxyl, amino, halo, nitro, cyano, carboxylic acid, alkyl, cycloalkyl, alkenyl, alkynyl, aryl, heteroaryl, hydroxyalkyl, alkoxy, C1-C8 acyl, haloalkyl, preferably $R^1$-$R^2$ represent hydrogen, alkyl, cycloalkyl or haloalkyl, more preferably hydrogen, methyl or $CF_3$.

According to a specific embodiment, Ar is optionally substituted and is selected from phenyl, pyridine, indole, indazole, 7-azaindole, quinoline, quinolinone, dihydroquinolinone, dihydroquinaolinone, imidazole, pyrrole, or pyrazol, benzimidazolone, benzoxazolone, benzimidazole-thione, benzotriazole, benimidazole, benzoxazinone, indolinedione, hydroxypyridinone, benzothiazolamine. In a preferred embodiment, Ar is a phenyl group, optionally substituted. In one embodiment, when Ar is substituted, it is preferably substituted by one or more group selected from F, Cl, Br, $NO_2$, $NH_2$, $NMe_2$, OH, OMe, $CH_3$ or $CF_3$. In a specific embodiment, when Ar is substituted, it is preferably substituted by one or more group selected from OH, hydroxyalkyl, aminoacid, carbamate, carbonate, ester, thioester, phosphonate, phosphonate methyloxy, phosphonate methylamino, alkoxy and alkylthio.

According to a specific embodiment, Ar is a phenol group or a bio-isostere thereof, wherein preferred phenol bio-isosteres are selected from:

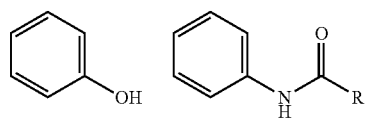

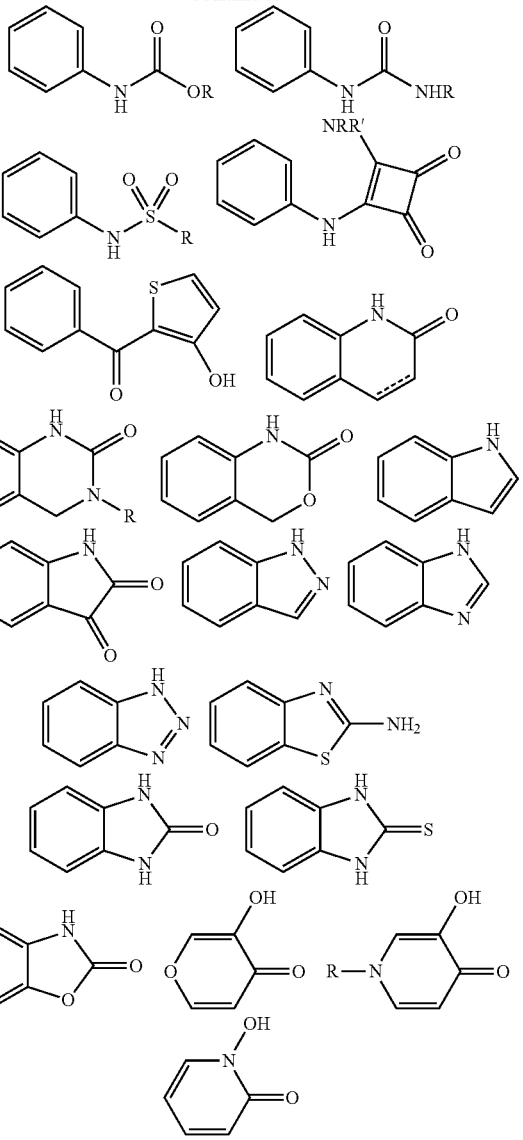

wherein R and R' are preferably selected from hydrogen, alkyl, cycloalkyl, alkenyl, alkynyl, aryl, heteroaryl, alkylaryl, alkylheteroaryl.

According to a specific embodiment, Ar is a phenol group or a prodrug thereof. Preferably, the prodrug of the phenol group is selected from aminoacid, carbamate, carbonate, ester, thioester, phosphonate, phosphonate methyloxy, phosphonate methylamino, alkyloxy and alkylthio groups.

According to a specific embodiment, in compounds of Formula I, $R^2$ represents H.

According to a specific embodiment, in compounds of Formula I, $R^2$ represents an hydrogen atom or a group selected from hydroxyl, amino, halo, nitro, cyano, carboxylic acid, alkyl, cycloalkyl, alkenyl, alkynyl, aryl, heteroaryl, hydroxyalkyl, alkoxy, C1-C8 acyl, haloalkyl; provided that $R^2$ is not methyl.

According to a specific embodiment, in compounds of the invention, $R^1$ represents an alkyl group or a haloalkyl group. According to a specific embodiment, in compounds of Formula I, $R^1$ represents an alkyl group, preferably a methyl.

According to a specific embodiment, in compounds of Formula I, $R^1$ represents a haloalkyl group, preferably a trifluoromethyl.

According to a specific embodiment, in compounds of the invention, $R^1$ represents an alkyl group, preferably methyl, and $R^2$ represents a hydrogen atom. According to a specific embodiment, in compounds of the invention, $R^1$ represents a haloalkyl group, preferably trifluoromethyl, and $R^2$ represents a hydrogen atom.

According to an embodiment, compounds of Formula I the invention as described above are of Formula Ia:

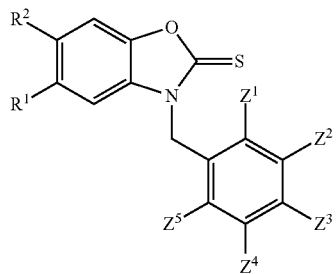

and pharmaceutically acceptable enantiomers, salts or solvates thereof, wherein:

$R^1$-$R^2$ are the same or different and represent a hydrogen atom or a group selected from hydroxyl, amino, halo, nitro, cyano, carboxylic acid, alkyl, cycloalkyl, alkenyl, alkynyl, aryl, heteroaryl, hydroxyalkyl, alkoxy, C1-C8 acyl, haloalkyl, preferably $R^1$-$R^2$ represent hydrogen, alkyl, cycloalkyl or haloalkyl, more preferably hydrogen, methyl or $CF_3$;

$Z^1$ represents a hydrogen atom or a group selected from halo, hydroxyl, hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, 3-hydroxythiophen-2-yl-metanone, or form with $Z^2$ an aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; preferably $Z^1$ represents a hydrogen atom or a group selected from halo, hydroxyl, nitro, amino, amido, carbamate, carbamide, sulfonamide, alkoxy, alkyl, haloalkyl, alkenyl, alkynyl, aryl, heteroaryl, 4-amino-cyclobut-3-ene-1,2-dione, 3-hydroxythiophen-2-yl-metanone, or form with $Z^2$ an aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; more preferably $Z^1$ represents H, F, Cl, Br, $NO_2$, $NH_2$, $NMe_2$, OH, OMe, $CH_3$ or $CF_3$;

$Z^2$ represents a hydrogen atom or a group selected from halo, hydroxyl hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, 3-hydroxythiophen-2-yl-metanone, or form with $Z^1$ or $Z^3$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; preferably $Z^2$ represents a hydrogen atom or a group selected from halo, hydroxyl, nitro, amino, amido, carbamate, carbamide, sulfonamide, alkoxy, alkyl, haloalkyl, alkenyl, alkynyl, aryl, heteroaryl, 4-amino-cyclobut-3-ene-1,2-dione, 3-hydroxythiophen-2-yl-metanone, or form with $Z^1$ or $Z^3$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; more preferably $Z^2$ represents H, F, Cl, Br, $NO_2$, $NH_2$, $NMe_2$, OH, OMe, $CH_3$ or $CF_3$;

$Z^3$ represents a hydrogen atom or a group selected from halo, hydroxyl, hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, 3-hydroxythiophen-2-yl-metanone, or form with $Z^2$ or $Z^4$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; preferably $Z^3$ represents a hydrogen atom or a group selected from halo, hydroxyl, nitro, amino, amido, carbamate, carbamide, sulfonamide, alkoxy, alkyl, haloalkyl, alkenyl, alkynyl, aryl, heteroaryl, 4-amino-cyclobut-3-ene-1,2-dione, 3-hydroxythiophen-2-yl-metanone, or form with $Z^2$ or $Z^4$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; more preferably $Z^3$ represents H, F, Cl, Br, $NO_2$, $NH_2$, $NMe_2$, OH, OMe, $CH_3$ or $CF_3$;

$Z^4$ represents a hydrogen atom or a group selected from halo, hydroxyl, hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, 3-hydroxythiophen-2-yl-metanone, or form with $Z^3$ or $Z^5$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; preferably $Z^4$ represents a hydrogen atom or a group selected from halo, hydroxyl, nitro, amino, amido, carbamate, carbamide, sulfonamide, alkoxy, alkyl, haloalkyl, alkenyl, alkynyl, aryl, heteroaryl, 4-amino-cyclobut-3-ene-1,2-dione, 3-hydroxythiophen-2-yl-metanone, or form with $Z^3$ or $Z^5$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; more preferably $Z^4$ represents H, F, Cl, Br, $NO_2$, $NH_2$, $NMe_2$, OH, OMe, $CH_3$ or $CF_3$;

$Z^5$ represents a hydrogen atom or a group selected from halo, hydroxyl, hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, 3-hydroxythiophen-2-yl-metanone, or form with $Z^4$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; preferably $Z^5$ represents a hydrogen atom or a group selected from halo, hydroxyl, nitro, amino, amido, carbamate, carbamide, sulfonamide, alkoxy, alkyl, haloalkyl, alkenyl, alkynyl, aryl, heteroaryl, 4-amino-cyclobut-3-ene-1,2-dione, 3-hydroxythiophen-2-yl-metanone, or form with $Z^4$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; more preferably $Z^5$ represents H, F, Cl, Br, $NO_2$, $NH_2$, $NMe_2$, OH, OMe, $CH_3$ or $CF_3$.

According to an embodiment, compounds of Formula I the invention as described above are of Formula Ia':

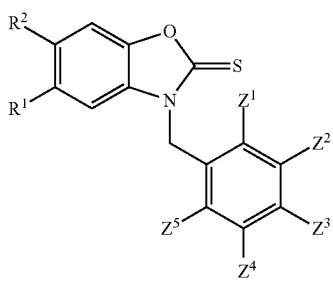

and pharmaceutically acceptable enantiomers, salts or solvates thereof, wherein:
- $R^1$-$R^2$ are the same or different and represent a hydrogen atom or a group selected from hydroxyl, amino, halo, nitro, cyano, carboxylic acid, alkyl, cycloalkyl, alkenyl, alkynyl, aryl, heteroaryl, hydroxyalkyl, alkoxy, C1-C8 acyl, haloalkyl, preferably $R^1$-$R^2$ represent hydrogen, alkyl, cycloalkyl or haloalkyl, more preferably hydrogen, methyl or $CF_3$;
- $Z^1$ represents a hydrogen atom or a group selected from halo, hydroxyl, nitro, amino, amido, carbamate, carbamide, sulfonamide, alkoxy, alkyl, haloalkyl, alkenyl, alkynyl, aryl, heteroaryl, 4-amino-cyclobut-3-ene-1,2-dione, 3-hydroxythiophen-2-yl-metanone, or form with $Z^2$ an aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; preferably $Z^1$ represents H, F, Cl, Br, $NO_2$, $NH_2$, $NMe_2$, OH, OMe, $CH_3$ or $CF_3$;
- $Z^2$ represents a hydrogen atom or a group selected from halo, hydroxyl, nitro, amino, amido, carbamate, carbamide, sulfonamide, alkoxy, alkyl, haloalkyl, alkenyl, alkynyl, aryl, heteroaryl, 4-amino-cyclobut-3-ene-1,2-dione, 3-hydroxythiophen-2-yl-metanone, or form with $Z^1$ or $Z^3$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; preferably $Z^2$ represents H, F, Cl, Br, $NO_2$, $NH_2$, $NMe_2$, OH, OMe, $CH_3$ or $CF_3$;
- $Z^3$ represents a hydrogen atom or a group selected from halo, hydroxyl, nitro, amino, amido, carbamate, carbamide, sulfonamide, alkoxy, alkyl, haloalkyl, alkenyl, alkynyl, aryl, heteroaryl, 4-amino-cyclobut-3-ene-1,2-dione, 3-hydroxythiophen-2-yl-metanone, or form with $Z^2$ or $Z^4$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; preferably $Z^3$ represents H, F, Cl, Br, $NO_2$, $NH_2$, $NMe_2$, OH, OMe, $CH_3$ or $CF_3$;
- $Z^4$ represents a hydrogen atom or a group selected from halo, hydroxyl, nitro, amino, amido, carbamate, carbamide, sulfonamide, alkoxy, alkyl, haloalkyl, alkenyl, alkynyl, aryl, heteroaryl, 4-amino-cyclobut-3-ene-1,2-dione, 3-hydroxythiophen-2-yl-metanone, or form with $Z^3$ or $Z^5$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; preferably $Z^4$ represents H, F, Cl, Br, $NO_2$, $NH_2$, $NMe_2$, OH, OMe, $CH_3$ or $CF_3$;
- $Z^5$ represents a hydrogen atom or a group selected from halo, hydroxyl, nitro, amino, amido, carbamate, carbamide, sulfonamide, alkoxy, alkyl, haloalkyl, alkenyl, alkynyl, aryl, heteroaryl, 4-amino-cyclobut-3-ene-1,2-dione, 3-hydroxythiophen-2-yl-metanone, or form with $Z^4$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; preferably $Z^5$ represents H, F, Cl, Br, $NO_2$, $NH_2$, $NMe_2$, OH, OMe, $CH_3$ or $CF_3$.

According to a specific embodiment, $Z^1$, $Z^3$, $Z^4$ and $Z^5$ represent H.

According to a preferred embodiment, $Z^2$ represents a group selected from halo, hydroxyl, nitro, amino, amido, carbamate, carbamide, sulfonamide, alkoxy, alkyl, haloalkyl, alkenyl, alkynyl, aryl, heteroaryl, 4-amino-cyclobut-3-ene-1,2-dione, 3-hydroxythiophen-2-yl-metanone, or form with $Z^1$ or $Z^3$ aryl ring, an heteroaryl ring, a cycloalkyl ring or a heterocyclyl, optionally substituted by one or more group selected from oxo, halo, hydroxyl, nitro, amino, alkoxy, alkyl, haloalkyl, alkenyl, alkynyl, aryl, heteroaryl; preferably $Z^2$ represents F, Cl, Br, $NO_2$, $NH_2$, $NMe_2$, OH, OMe, $CH_3$ or $CF_3$.

According to a specific embodiment, $Z^2$ represents a hydroxyl group. In this embodiment, $Z^1$, $Z^3$, $Z^4$ and $Z^5$ preferably represent hydrogen atoms. According to another specific embodiment, in compounds of the invention, $Z^2$ represents a hydroxyl group and $Z^3$ represents a halogen, preferably a fluorine atom. In this embodiment, $Z^1$, $Z^4$ and $Z^5$ preferably represent hydrogen atoms.

According to an embodiment, compounds of Formula Ia the invention as described above are of Formula Ib:

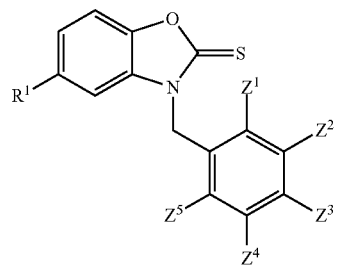

and pharmaceutically acceptable enantiomers, salts or solvates thereof, wherein $R^1$, $Z^1$, $Z^2$, $Z^3$, $Z^4$ and $Z^5$ are as defined above.

According to a preferred embodiment of the invention, compounds of Formula I of the invention are those listed in table below:

| Compound n° | Structure | Chemical name |
|---|---|---|
| 1 | 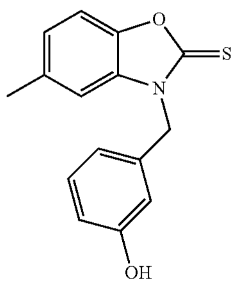 [SMILES: Cc1ccc2oc(=S)n(Cc3cccc(O)c3)c2c1] | 3-(3-hydroxybenzyl)-5-methylbenzo[d]oxazole-2(3H)-thione |
| 2 | 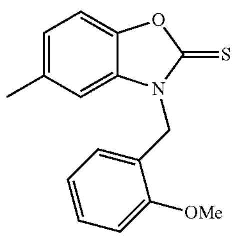 [SMILES: COc1ccccc1Cn1c(=S)oc2ccc(C)cc21] | 3-(2-methoxybenzyl)-5-methylbenzo[d]oxazole-2(3H)-thione |
| 3 | 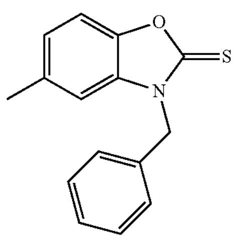 [SMILES: Cc1ccc2oc(=S)n(Cc3ccccc3)c2c1] | 3-benzyl-5-methylbenzo[d]oxazole-2(3H)-thione |
| 4 | 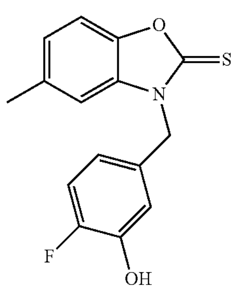 [SMILES: Cc1ccc2oc(=S)n(Cc3ccc(F)c(O)c3)c2c1] | 3-(4-fluoro-3-hydroxybenzyl)-5-methylbenzo[d]oxazole-2(3H)-thione |
| 5 | | 3-(4-fluoro-3-hydroxybenzyl)-5-(trifluoromethyl)benzo[d]oxazole-2(3H)-thione | or pharmaceutically acceptable enantiomers, salts and solvates thereof.

Compounds are named using ChemBioDraw® Ultra version 12.0 (PerkinElmer).

The compounds of Formula I and subformulae thereof may contain an asymmetric center and thus may exist as different stereoisomeric forms. Accordingly, the present invention includes all possible stereoisomers and includes not only racemic compounds but the individual enantiomers and their non-racemic mixtures as well. When a compound is desired as a single enantiomer, such may be obtained by stereospecific synthesis, by resolution of the final product or any convenient intermediate, or by chiral chromatographic methods as each are known in the art. Resolution of the final product, an intermediate, or a starting material may be performed by any suitable method known in the art.

The compounds of the present invention may be administered in the form of pharmaceutically acceptable salts.

The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations.

Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylene-diamine, chloroprocaine, diethanolamine, procaine, N-benzylphenethyl-amine, diethylamine, piperazine, tris(hydroxymethyl) aminomethane, and tetramethylammonium hydroxide. These salts may be prepared by standard procedures, e.g. by reacting a free acid with a suitable organic or inorganic base. Where a basic group is present, such as amino, an acidic salt, i.e. hydrochloride, hydrobromide, acetate, palmoate, and the like, can be used as the dosage form.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine, 2-(diethylamino)ethanol, ethanolamine, morpholine, 4-(2- hydroxyethyl)morpholine and zinc salts. Hemisalts of acids and bases may also be formed, for example, hemisulphate and hemicalcium salts. Preferred, pharmaceutically acceptable salts include hydrochloride/chloride, hydrobromide/bromide, bisulphate/sulphate, nitrate, citrate, and acetate.

When the compounds of the invention contain an acidic group as well as a basic group the compounds of the invention may also form internal salts, and such compounds are within the scope of the invention. When the compounds of the invention contain a hydrogen-donating heteroatom (e.g. NH), the invention also covers salts and/or isomers formed by transfer of said hydrogen atom to a basic group or atom within the molecule.

Pharmaceutically acceptable salts of compounds of Formula I may be prepared by one or more of these methods:
  (i) by reacting the compound of Formula I with the desired acid;
  (ii) by reacting the compound of Formula I with the desired base;
  (iii) by removing an acid- or base-labile protecting group from a suitable precursor of the compound of Formula I or by ring-opening a suitable cyclic precursor, for example, a lactone or lactam, using the desired acid; or
  (iv) by converting one salt of the compound of Formula I to another by reaction with an appropriate acid or by means of a suitable ion exchange column.

All these reactions are typically carried out in solution. The salt, may precipitate from solution and be collected by filtration or may be recovered by evaporation of the solvent. The degree of ionization in the salt may vary from completely ionized to almost non-ionized.

In addition, although generally, with respect to the salts of the compounds of the invention, pharmaceutically acceptable salts are preferred, it should be noted that the invention in its broadest sense also included non-pharmaceutically acceptable salts, which may for example be used in the isolation and/or purification of the compounds of the invention. For example, salts formed with optically active acids or bases may be used to form diastereoisomeric salts that can facilitate the separation of optically active isomers of the compounds of Formula I above.

Also, in the case of an alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

All references to compounds of Formula I include references to enantiomers, salts, solvates, polymorphs, multi-component complexes and liquid crystals thereof.

The compounds of the invention include compounds of Formula I as hereinbefore defined, including all polymorphs and crystal habits thereof, prodrugs and isomers thereof (including optical, geometric and tautomeric isomers) and isotopically-labeled compounds of Formula I.

The invention also generally covers all pharmaceutically acceptable predrugs and prodrugs of the compounds of Formula I.

In one embodiment, the compound of the invention is for curing PH. Preferably, the compound of the invention slows down or stops the progression, aggravation, or deterioration of one or more symptoms of pulmonary hypertension; brings about ameliorations of the symptoms of pulmonary hypertension; and/or reduces the severity or incidence of pulmonary hypertension.

In one embodiment, the compound of the invention is for preventing, reducing or alleviating the symptoms associated with PH. In one embodiment, the alleviation or reduction of a symptom associated with PH corresponds to a diminution of shortness of breath, dizziness, fainting and/or leg swelling.

In one embodiment, the use of the compound of general Formula I is for an acute treatment of PH. In one embodiment, the use of the compound of general Formula I is for treating an acute form of PH.

In another embodiment, the use of the compound of general Formula I is for a chronic treatment of PH. In another embodiment, the use of the compound of general Formula I is for treating a chronic form of PH.

PH is a disorder characterized by an increase of blood pressure in pulmonary arteries, pulmonary veins, or pulmonary capillaries, together known as the lung vasculature, leading to shortness of breath, dizziness, fainting, leg swelling and other symptoms.

PH as used herein may refer to the classification of diseases or conditions described in Simonneau et al. (J Am Coll Cardiol 2013 Dec. 24; 62(25 Suppl):D34-41). Should the classification change, the skilled artisan will know how to adapt the modifications of the classification to recognize the disease or condition of the present application.

Group 1 of this classification refers to pulmonary arterial hypertension (PAH) but is not limited to: Idiopathic PAH (wherein there is neither a family history of PAH nor an identified risk factor) and heritable PAH (germline mutations in the Bone Morphogenetic Protein Receptor-type 2 (BMPR2) gene; mutations in Activin Receptor-Like Kinase type 1 (ACVRL1 or ALK1), or Endoglin (ENG), or Caveolin-1 (CAV1), or Potassium Channel Subfamily K Member 3 (KCNK3), or other unknown genes); drug- and toxin-induced PAH; PAH associated with connective tissue diseases; PAH complication of HIV infection; portal hypertension; congenital heart diseases (CHD); schistosomiasis.

Group 1' of this classification refers to pulmonary veno-occlusive disease (PVOD) and/or pulmonary capillary hemangiomatosis (PCH).

Group 1" of this classification refers to persistent PH of the newborn (PPHN).

Group 2 of this classification refers to left heart disease.

Group 3 of this classification refers to lung disease and/or hypoxia.

Group 4 of this classification refers to chronic thromboembolic pulmonary hypertension (CTEPH).

Group 5 of this classification refers to PH for which the etiology is unclear or multifactorial such as: hematologic disorders (chronic hemolytic anemia, myeloproliferative disorders, splenectomy); systemic disorders such as, for example, Sarcoidosis, Pulmonary Langerhans cell histiocytosis, Lymphangioleiomyomatosis; metabolic disorders such as glycogen storage disease, Gaucher disease, thyroid disorders; miscellaneous conditions such as, for example, tumor obstruction, pulmonary artery sarcomas, occlusion of the microvasculature by metastatic tumor emboli, mediastinal fibrosis, end-stage renal disease.

In one embodiment, PH is selected from Groups 1, 1', 1", 2, 3, 4 or 5; preferably, PH is selected from Groups 1, 1', 1", 2, 4 or 5; more preferably, PH is selected from Group 1 or Group 4, more preferably PH is selected from Group 1, i.e. PH is pulmonary arterial hypertension. In one embodiment, PH is not related to hypoxia.

Examples of causes of PH include, but are not limited to a combination of one or several of these phenomena: a complex interplay between pulmonary endothelial dysfunction and inflammation; and/or an abnormal pulmonary endothelial dysfunction; and/or a chronic inflammation with an increased secretion of pro-inflammatory cytokines, chemokines and presence of macrophages, monocytes, and T and B lymphocytes; and/or loss of pulmonary vessels; and/or an abnormal smooth muscle hyperplasia/hypertrophy, an aberrant extracellular matrix (ECM) remodeling; and/or a specific genetic and/or environmental predisposing factors; and/or another unknown phenomena. In addition, imbalances in vasoactive mediators are a central feature of the dysfunctional pulmonary vascular endothelium in PH: for example, vasoconstrictive agents thromboxane and endothelin-1 are found to be significantly up-regulated in pulmonary arteries which induce proliferation of pulmonary vascular cells (such as pulmonary artery smooth muscles and endothelial cells). Consequently these phenomena in association with other abnormalities cause remodeling of the vessels, associated or not with obliteration of pulmonary vessels and formation of plexiform lesions. This marked pulmonary vascular remodeling leads to sustained elevation of pulmonary vascular resistance (reflected by increase in mean pulmonary artery pressure ≥25 mmHg at rest, ≥30 mmHg during exercise) and progressive right-heart failure.

In one embodiment, PH is selected from the list comprising or consisting of idiopathic pulmonary arterial hypertension, heritable pulmonary arterial hypertension, familial pulmonary arterial hypertension, or associated pulmonary hypertension (in particular associated pulmonary arterial hypertension) with other diseases, persistent pulmonary hypertension of the newborn, pulmonary veno-occlusive disease (PVOD) and/or pulmonary capillary hemangiomatosis (PCH), pulmonary hypertension owing to left heart disease such as systolic dysfunction, diastolic dysfunction, valvular heart disease, pulmonary hypertension owing to lung disease and/or hypoxia such as chronic obstructive pulmonary disease, interstitial lung disease, other pulmonary diseases with mixed restrictive and obstructive pattern, sleep-disordered breathing, alveolar hypoventilation disorders, chronic exposure to high altitude, developmental abnormalities, chronic thromboembolic pulmonary hypertension (CTEPH), pulmonary hypertension with unclear multifactorial mechanisms, hematologic diseases (such as, for example, myeloproliferative disease, splenectomy), systemic diseases (such as, for example, sarcoidosis), pulmonary Langerhans cell histiocytosis (such as, for example, lymphangioleiomyomatosis, neurofibromatosis, vasculitis), metabolic disorders (such as, for example, glycogen storage disease, Gaucher disease, thyroid diseases), tumoral obstruction, fibrosing mediastinitis, and chronic renal failure on dialysis.

Examples of diseases which may be associated with pulmonary hypertension, in particular with pulmonary arterial hypertension (which may be referred as PH associated diseases, disorders or conditions) include but are not limited to: connective tissue disease, systemic sclerosis, lung fibrosis, bronchiectasis, hypoxia, hypoxemia, hypocapnia, chronic myoproliferative disorders, emphysema, diastolic left heart dysfunction, Sjögren syndrome, polymyositis, rheumatoid arthritis, collagen vascular disease (e.g. scleroderma), hereditary hemorrhagic telangiectasia, congenital shunts between the systemic and pulmonary circulation, portal hypertension, congenital heart disease, Eisenmenger syndrome, schistosomiasis, chronic hemolytic anemia, neurofibromatosis type 1, Recklinghausen disease, Gaucher disease, thyroid diseases, HIV infection, drugs, and toxins increasing the risk of developing pulmonary hypertension. In one embodiment, the compound of the invention inhibits the pulmonary vascular cell proliferation connected to or within the lungs or vessel walls as described in Example 2.

Technics to measure cell proliferation, survival, migration, and differentiation are well known by the skilled artisan. Among them, measurements of 5-bromo-2-deoxyuridine (BrdU) incorporation, cell counting, caspase-3 activity, immunostaining for proliferating cell nuclear antigen (PCNA), terminal deoxynucleotidyl transferase dUTP nick end labeling (TUNEL), Ki68, phosphorylation state of ERK/MAPK, PI3K-akt, Src signaling pathways can be indicative of cell proliferation and survival.

In another embodiment, the compound of the invention inhibits the inflammation and/or autoimmunity mechanisms within the lungs. Technics to determine an inflammation and/or autoimmunity are well known by the skilled artisan. Among them, measurements of cytokines release, determination of phosphorylated kinases involved in inflammatory mechanisms (ERK/MAPK, NFκB pathways) or presence of immune cells, autoantibodies, analysis of regulatory T cell (Treg) function can be indicative of an inflammation/autoimmunity.

In another embodiment, the compound of the invention inhibits tautomerase activity reflecting an inhibitory effect on the MIF CD74 axis. An example of a technic to determine the activity of MIF is described in Biological Example 1 of the present application. Circulating MIF can also be evaluated by immunoassay. Other technics are well known in the state of the art.

The present invention further relates to a composition comprising, or consisting of, a compound of general Formula I for treating, or for use in the treatment of PH.

The present invention relates to a composition consisting essentially of a compound of general Formula I. As used herein, "consisting essentially of" means that the compound of general Formula I is the unique therapeutic agent within the composition.

The present invention also relates to a pharmaceutical composition comprising or consisting of a compound of general Formula I or the composition of the invention and at least one pharmaceutically acceptable excipient.

The present invention also relates to a medicament comprising or consisting of, a compound of general Formula I or the composition of the invention.

The present invention relates to a composition, a pharmaceutical composition or a medicament comprising a therapeutically effective amount of a compound of general Formula I.

In one embodiment, a therapeutically effective amount of the compound of the invention ranges from about 0.01 mg to about 500 mg, preferably from about 0.05 mg to about 100 mg, more preferably from about 0.1 mg to about 50 mg and even more preferably from about 0.5 mg to about 10 mg.

In one embodiment, the composition, pharmaceutical composition or medicament of the invention comprises an amount of a compound of Formula I ranging from about 1 pM to about 1 mM, preferably from about 10 pM to about 50 μM, more preferably from about 0.1 nM to about 1 μM, even more preferably from about 0.5 nM to about 0.1 μM, and still even more preferably is of about 1 nM.

In one embodiment of the invention, the therapeutically effective amount of the compound of the invention corresponds to the amount to be administered to a subject in need thereof for reaching amelioration in the patient's World Health Organization (WHO) functional class and/or an measurable decrease in the value of the mean pulmonary arterial pressure (mPAP) measured in a healthy subject, wherein the mPAP measured in a healthy subject may range from about 11 to about 17 mmHg, preferably is of about 14 mmHg.

In one embodiment, the therapeutically effective amount is administered once a month, once a week, twice a week, at least once a day, twice, or three times a day.

In another embodiment, the therapeutically effective amount is administered once a day on consecutive days for at least a week, at least a month, at least a year, or on as needed basis for the rest of the patient's life.

In another embodiment, the therapeutically effective amount is administered once a week on consecutive weeks for at least two weeks, one month, at least a year, or on as needed basis for the rest of the patient's life.

In another embodiment, the therapeutically effective amount is administered once a month on consecutive months for at least two months, a year, or on as needed basis for the rest of the patient's life.

In another embodiment, the therapeutically effective amount is administered at least once a day, twice or three times a day to a subject until the patient's World Health Organization (WHO) functional class and/or the mean pulmonary arterial pressure (mPAP) decreases to about 11 to 17 mmHg, preferably about 14 mmHg followed by an administration maintaining the pulmonary arterial pressure from about 11 to 17 mmHg, preferably about 14 mmHg at least once a day, every other days, every three days, every week or every month as needed for the rest of his life.

It will be understood that the therapeutic amount of the compounds and compositions of the present invention will be decided by the attending physician within the scope of sound medical judgment. The specific therapeutically effective amount for any particular subject will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific peptide employed; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may vary over a wide range from 0.01 to 1,000 mg per adult per day. A medicament typically contains from about 0.01 mg to about 500 mg of the active ingredient. An effective amount of the drug is ordinarily supplied at a dosage level from 0.0002 mg/kg to about 30 mg/kg of body weight per day.

In one embodiment, a therapeutically effective amount of the compound of the invention ranges from about 1 to about 50 mg/kg of body weight, preferably from about 5 to about 30 mg/kg of body weight, most preferably from about 10 to 20 mg/kg of body weight.

In one embodiment, a therapeutically effective amount of the compound of the invention ranges from about 1 to about 50 mg/kg of body weight/day, preferably from about 5 to about 30 mg/kg of body weight/day, most preferably from about 10 to 20 mg/kg of body weight/day.

The composition, pharmaceutical composition or medicament of the invention is administered, or is to be administered by several routes of administration. Examples of adapted routes of administration include, but are not limited to, subcutaneous, intramuscular, intravenous, transdermal, topical, nasal and oral administration, or injection. The type of form for administration will be matched to the disease or disorder to be treated. Preferably, the pharmaceutical composition or medicament of the invention is administered, or is to be administered by intravenous administration, oral administration or intratracheal administration.

In one embodiment, the composition, pharmaceutical composition or medicament of the invention is in a form adapted for injection, preferably selected from the group comprising solutions, such as, for example, sterile aqueous solutions, dispersions, emulsions, suspensions, solid forms suitable for using to prepare solutions or suspensions upon the addition of a liquid prior to use, such as, for example, powder, liposomal forms and the like.

In another embodiment, the composition, pharmaceutical composition or medicament of the invention is in a form adapted to oral administration. According to a first embodiment, the form adapted to oral administration is a solid form selected from the group comprising tablets, pills, capsules, soft gelatin capsules, sugar-coated pills, orodispersing tablets, effervescent tablets or other solids. According to a second embodiment, the form adapted to oral administration is a liquid form, such as, for example, a drinkable solution, a buccal spray, liposomal forms and the like. The oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

In another embodiment, the composition, pharmaceutical composition or medicament of the invention is in a form adapted to nasal administration. The form adapted to nasal administration is a liquid or inhaling form for example as a nasal spray/aerosol device.

The present invention thus also relates to a composition for use in the treatment of PH as described here above, wherein the composition comprises a compound of general Formula I in a form suitable for nasal administration.

In one embodiment of the invention, the compound or the composition is administered to the subject by respiratory administration, preferably by inhalation.

These administration routes may increase the bioavailability of the active agent compared to other administration route and may thus be of interest for treating subjects that may suffer from lungs.

In another embodiment, the composition, pharmaceutical composition or medicament of the invention is in a form adapted to intratracheal administration. In another embodiment, the composition, pharmaceutical composition or medicament of the invention is delivered in a form adapted for inhaling administration such as an aerosol form, to the upper nasal epithelia of the patient. In another embodiment, the composition, pharmaceutical composition or medicament of the invention is delivered in a form adapted for intranasal administration, such as an aerosol form, to the nasal olfactory epithelia of the patient.

Another object of the invention is a device comprising a compound of Formula I for nasal administration or for respiratory administration of said compound for use in the treatment of PH.

In one embodiment, the compound or the composition of the invention may be delivered by any of a variety of inhalation devices known in the art for administration of a therapeutic agent by inhalation. These devices include metered dose inhalers, nebulizers, dry powder inhalers, sprayers, and the like.

Some specific examples of commercially available inhalation devices suitable for the practice of this invention are Cyclohaler, Turbohaler™ (Astra), Rotahaler® (Glaxo), Diskus® (Glaxo), Spiros™ inhaler (Dura), devices marketed by Inhale Therapeutics, AERx™ (Aradigm), the Ultravent® nebulizer (Mallinckrodt), the Acorn II® nebulizer (Marquest Medical Products), the Ventolin® metered dose inhaler (Glaxo), the Spinhaler® powder inhaler (Fisons), or the like.

As those skilled in the art will recognize, the formulation of the compound or the composition of the invention, the quantity of the formulation delivered and the duration of administration of a single dose depend on the type of inhalation device employed. For some aerosol delivery systems, such as nebulizers, the frequency of administration and length of time for which the system is activated will depend mainly on the concentration of the compound or the composition of the invention in the aerosol. For example, shorter periods of administration can be used at higher concentrations of the compound or the composition of the invention in the nebulizer solution. Devices such as metered dose inhalers can produce higher aerosol concentrations, and can be operated for shorter periods to deliver the desired amount of the compound or the composition of the invention. Devices such as powder inhalers deliver active agent until a given charge of agent is expelled from the device. In this type of inhaler, the amount of the compound or the composition of the invention in a given quantity of the powder determines the dose delivered in a single administration.

In one embodiment, particles of the compound or the composition of the invention delivered by inhalation have a particle size preferably less than about 10 µm, more preferably in the range of about 1 µm to about 5 µm.

Advantageously for administration as a dry powder the compound or the composition of the invention is prepared in a particulate form with a particle size of less than about 10 µm, preferably from about 1 to about 5 µm. Such formulations may be achieved by spray drying, milling, micronisation, or critical point condensation of a solution containing the compound or the composition of the invention and other desired ingredients.

Formulations of the compound or the composition of the invention for administration from a dry powder inhaler typically include a finely divided dry powder containing the compound or the composition of the invention, but the powder can also include a bulking agent, carrier, excipient, another additive, or the like. Examples of additives include, but are not limited to, mono-, di-, and polysaccharides; sugar alcohols and other polyols, such as, for example, lactose, glucose, raffinose, melezitose, lactitol, maltitol, trehalose, sucrose, mannitol, starch, or combinations thereof; surfactants, such as sorbitols, dipalmitoylphosphatidyl choline, or lecithin; or the like.

A spray including the compound or the composition of the invention can be produced by forcing a suspension or solution of the compound or the composition of the invention through a nozzle under pressure. The nozzle size and configuration, the applied pressure, and the liquid feed rate can be chosen to achieve the desired output and particle size. An electrospray can be produced, e.g., by an electric field in connection with a capillary or nozzle feed. Formulations of the compound or the composition of the invention suitable for use with a sprayer will typically include the compound or the composition of the invention in an aqueous solution.

The formulation may include agents such as an excipient, a buffer, an isotonicity agent, a preservative, a surfactant, and zinc. The formulation can also include an excipient or agent for stabilization of the compound or the composition of the invention, such as a buffer, a reducing agent, a bulk protein, or a carbohydrate. Examples of bulk proteins include, but are not limited to, albumin, protamine, or the like. Examples of carbohydrates include, but are not limited to sucrose, mannitol, lactose, trehalose, glucose, or the like. The formulation of the compound or the composition of the invention can also include a surfactant, which can reduce or prevent surface-induced aggregation of the compound or composition of the invention caused by atomization of the solution in forming an aerosol. Various conventional surfactants can be employed, such as polyoxyethylene fatty acid esters and alcohols, and polyoxyethylene sorbitol fatty acid esters.

In another embodiment, the composition, pharmaceutical composition or medicament of the invention is in a form adapted for local delivery.

In another embodiment, the composition, pharmaceutical composition or medicament of the invention is in a form adapted to topical administration. Examples of formulations adapted to topical administration include, but are not limited to, ointment, paste, eye drops, cream, patch, such as, for example, transdermal patch, gel, liposomal forms and the like.

In another embodiment, the composition, pharmaceutical composition or medicament of the invention is in the form of, or comprises, liposomes and/or nanoparticles.

In another embodiment, the composition, pharmaceutical composition or medicament of the invention further comprises some excipients, such as, for example, surfactants (e.g. hydroxypropylcellulose); suitable carriers, such as, for example, solvents and dispersion media containing, for example, water, saline (such as, for example, phosphate buffered saline (PBS), ethanol, polyol (e.g. glycerol, propylene glycol, and liquid polyethylene glycol, and the like), suitable mixtures thereof, and vegetable oils, such as, for example, peanut oil and sesame oil; isotonic agents, such as, for example, sugars or sodium chloride; coating agents, such as, for example, lecithin; agents delaying absorption, such as, for example, aluminum monostearate and gelatin; preservatives, such as, for example, benzalkonium chloride, benzethonium chloride, chlorobutanol, thimerosal and the like; buffers, such as, for example, boric acid, sodium and potassium bicarbonate, sodium and potassium borates, sodium and potassium carbonate, sodium acetate, sodium biphosphate and the like; tonicity agents, such as, for example, dextran 40, dextran 70, dextrose, glycerin, potassium chloride, propylene glycol, sodium chloride; antioxidants and stabilizers, such as, for example, sodium bisulfite, sodium metabisulfite, sodium thiosulfite, thiourea and the like; nonionic wetting or clarifying agents, such as, for example, polysorbate 80, polysorbate 20, poloxamer 282 and tyloxapol; viscosity modifying agents, such as, for example dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose; and the like.

In one embodiment, the composition, the pharmaceutical composition or the medicament of the invention is sterile. Advantageously, it comprises a preservative in order to prevent the growth of microorganisms. The prevention of the action of microorganisms may be brought about by various antibacterial and antifungal agents, such as, for example, parabens, chlorobutanol, phenol, sorbic acid, thimerosal, and the like.

In one embodiment, the form of the pharmaceutical compositions, the route of administration, the dosage and the regimen naturally depend upon the condition to be treated, the age, weight, and sex of the patient, etc, and may be easily determined by the skilled artisan.

In another embodiment of the invention, the administration dose of the composition, the pharmaceutical composition or the medicament is determined by the skilled artisan and personally adapted to each subject and/or the severity of the disease.

In one embodiment, a therapeutically effective amount of the composition, the pharmaceutical composition or the medicament of the invention is to be administered alone, i.e. is not administered in combination with another therapeutic agent for treating PH.

In one embodiment, the composition, the pharmaceutical composition or the medicament of the present invention is to be administered with other active agents. In one embodiment, the composition, the pharmaceutical composition or the medicament and the other active agent may be administered separately or in conjunction.

The present application relates also to the composition, the pharmaceutical composition or the medicament to be administered in combination with other active agents approved for the treatment of PH, for the treatment of a PH associated condition, or for the treatment of a disorder disclosed herein, or a combination thereof.

In another embodiment, a therapeutically effective amount of the composition, the pharmaceutical composition or the medicament of the invention is to be administered in combination with an effective amount of one or more other active agent(s), such as, for example, agents that may be used for treating PH.

In one embodiment, a therapeutically effective amount of the compound, composition, pharmaceutical composition or medicament of the invention is administered or is to be administered separately or in conjunction with one or more other active agent(s). In another embodiment, the administration of the compound, composition, pharmaceutical composition or medicament of the invention may be prior to, concurrent to, or subsequent to the administration of other active agent(s).

In another embodiment, a therapeutically effective amount of the composition, the pharmaceutical composition or the medicament of the invention is administered or is to be administered to a subject in periods of pre-exposure and/or post-exposure with other active agent(s).

Examples of other active agents include, but are not limited to, lipid-lowering agents such as HMG-CoA (3-hydroxy-3-methylglutaryl-coenzyme A); coronary/vasodilators such as ACE (angiotensin converting enzyme); angiotensin II receptor antagonists; adrenoceptor antagonists, alpha1-adrenoceptor antagonists, diuretics, calcium channel blockers, agents which cause an increase in cyclic guanosine monophosphate (cGMP), such as stimulators of soluble guanylate cyclase; plasminogen activators (thrombolytics/fibrinolytics) and thrombolysis/fibrinolysis compounds as inhibitors of plasminogen activator inhibitor (PAI inhibitors) or inhibitors of thrombin-activated fourth fibrinolysis inhibitor (TAFI inhibitors); anticoagulatory substances; anti-platelet agents (platelet aggregation inhibitors, platelet aggregation inhibitors); fibrinogen receptor antagonists; antiarrhythmics; kinase inhibitors; stimulators and activators of soluble guanylate cyclase; prostacyclin analogs and derivatives; endothelin receptor antagonists (ERAs); phosphodiesterase inhibitors; anti-inflammatory drugs such as antagonists of chemokine receptors, steroids, non-steroidal glucocorticoid receptor agonists; LTD4 antagonists, adenosine A2B receptor antagonists, β-2 adrenoceptor agonists; bronchodilatory drugs; antihistamine drug substances; nitric oxide donors (NO/nucleophile adducts-NONOates); phosphodiesterase (PDEs) inhibitors, neutral endopeptidase inhibitors such as neutral endopeptidase 1 inhibitors; anti-inflammatory drugs including antagonists of chemokine receptors; steroids; bronchodilatory drugs including anticholinergic or antimuscarinic agents, dual anti-inflammatory and bronchodilatory drugs including dual β-2 adrenoceptor agonist/muscarinic antagonists; antihistamine drug substances; agents that induce pulmonary vascular vasodilation; agents that are tryptophan hydroylase 1 (TPH1) inhibitors; multi-kinase inhibitors.

According to one embodiment, endothelin receptor antagonists (ERAs) are selected from bosentan, ambrisentan and macitentan.

According to one embodiment, prostacyclin analogs and derivatives are selected from epoprostenol (preferably a sodium salt thereof), iloprost trometamol and treprostinil (preferably a sodium salt thereof).

According to one embodiment, phosphodiesterase (PDEs) inhibitors are selected from sildenafil citrate and tadalafil.

According to one embodiment, agents which cause an increase in cyclic guanosine monophosphate (cGMP) are stimulators of soluble guanylate cyclase, preferably riociguat.

Examples of other active agents include, but are not limited to other MIF-inhibitors, such as, for example, ISO-1, ISO-92, and MIF-inhibitors described in WO2010/021693, WO2006/045505, WO2007/070961, US2012/039914, US2013/225586 and US2013/190369 (incorporated herein by reference).

In one embodiment, said other MIF-inhibitor is a heterocyclic compound as described in WO2010/021693. Examples of such heterocyclic compounds include, but are not limited to, compounds of general Formula B:

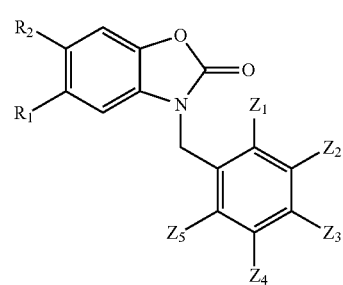

wherein $Z_4$ and $Z_5$ are H and wherein $R_1$, $R_2$, $Z_1$, $Z_2$ and $Z_3$ are as described in the Table below:

| Other MIF-inhibitor | $R_1$ | $R_2$ | $Z_1$ | $Z_2$ | $Z_3$ |
|---|---|---|---|---|---|
| 1' | CH₃ | H | H | H | H |
| 2' | H | CH₃ | H | H | H |
| 3' | OCH₃ | H | H | OCH₃ | H |
| 4' | CH₂OH | H | H | OCH₃ | H |
| 5' | CH₃ | H | H | OCH₃ | H |
| 6' | CH₃ | H | OCH₃ | H | H |

-continued

| Other MIF-inhibitor | $R_1$ | $R_2$ | $Z_1$ | $Z_2$ | $Z_3$ |
|---|---|---|---|---|---|
| 7' | $CH_3$ | H | $OCH_3$ | $OCH_3$ | H |
| 8' | F | H | H | H | H |
| 9' | F | H | H | H | $OCH_3$ |
| 10' | F | H | $OCH_3$ | H | H |
| 11' | OH | H | H | $OCH_3$ | H |
| 12' | OH | H | $OCH_3$ | H | H |
| 13' | OH | H | $OCH_3$ | $OCH_3$ | H |
| 14' | H | OH | H | H | H |
| 15' | H | OH | H | H | $OCH_3$ |
| 16' | H | OH | $OCH_3$ | H | H | or compounds having the following Formula:

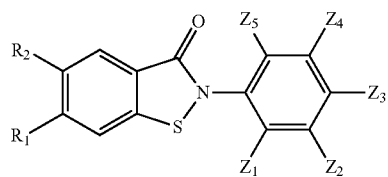

or compounds having the following Formula:

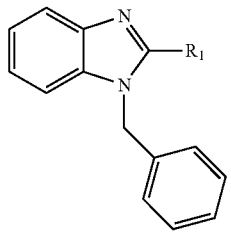

wherein $Z_4$ and $Z_5$ are H and wherein $R_1$, $R_2$, $Z_1$, $Z_2$ and $Z_3$ are as described in the Table below:

| Other MIF-inhibitor | $R_1$ | $R_2$ | $Z_1$ | $Z_2$ | $Z_3$ |
|---|---|---|---|---|---|
| 17' | F | H | H | H | $OCH_3$ |
| 18' | F | H | H | $OCH_3$ | H |
| 19' | F | H | H | $CH_2OH$ | H |
| 20' | H | F | H | H | Cl |
| 21' | H | Cl | $OCH_3$ | H | H |
| 22' | H | F | H | OH | H |
| 23' | F | H | H | $CH_2OAc$ | H |
| 24' | F | $NO_2$ | H | H | Cl |
| 25' | H | $CF_3$ | H | H | Cl |
| 26' | Br | H | H | H | Cl |
| 27' | CN | H | H | H | Cl |
| 28' | H | Br | H | H | Cl | or compounds of Formula:

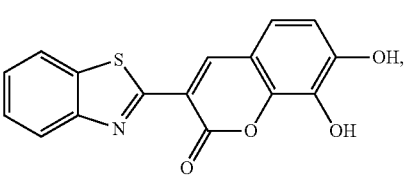

wherein $R_1$ is 4-thiazole, (2-pyridinyl)methyl, nitrile, amide, N, N—, dimethylamide, N-methylamide or $CH_3OCH_2CH_2$, or compounds having the following Formula:

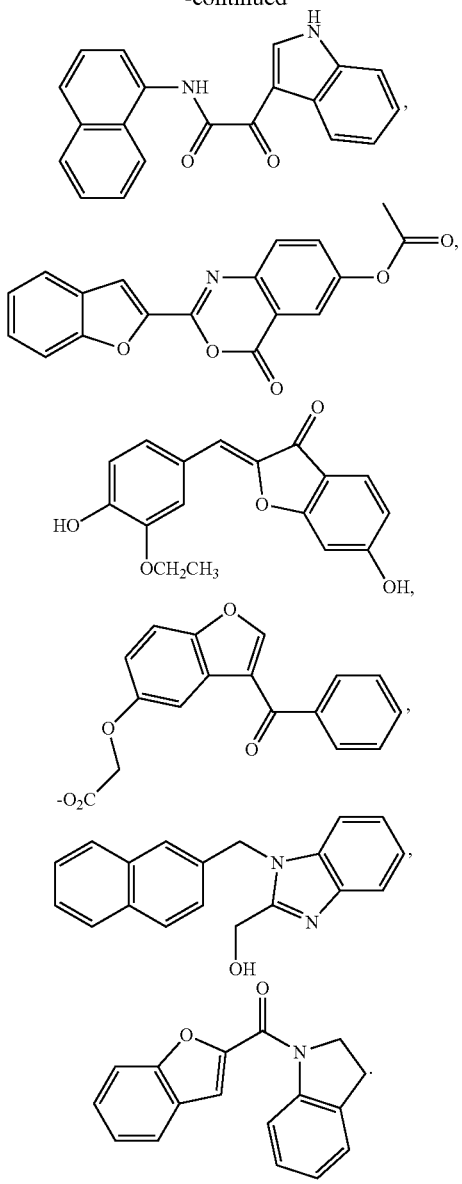

In one embodiment, said other MIF-inhibitor is a 3,4-dihydro-benzo[e][1,3]oxazin-2-one which is substituted at the nitrogen atom by unsubstituted or substituted (C3-8) cycloalkyl, (C1-4)alkyl(C3-8)cycloalkyl, (C6-18)aryl or (C6-18)aryl(C1-4)alkyl, as described in WO2006/045505. Examples of such compounds include, but are not limited to, 3-(phenyl)-3,4-dihydro-benzo[e][1,3]oxazin-2-ones, 3-(naphthyl)-3,4-dihydro-benzo[e][1,3]oxazin-2-ones, 3-(cyclohexyl)-3,4-dihydro-benzo[e][1,3]oxazin-2-ones, 3-(benzyl)-3,4-dihydro-benzo[e][1,3]oxazin-2-ones, 3-(phenyl)-7-hydroxy-3,4-dihydro-benzo[e][1,3]oxazin-2-ones, 3-(naphthyl)-7-hydroxy-3,4-dihydro-benzo[e][1,3]oxazin-2-ones, 3-(cyclohexyl)-7-hydroxy-3,4-dihydro-benzo[e][1,3]oxazin-2-ones, 3-(benzyl)-7-hydroxy-3,4-dihydro-benzo[e][1,3]oxazin-2-ones, 3-(phenyl)-7-aminosulfonyloxy-3,4-dihydro-benzo[e][1,3]oxazin-2-ones, 3-(naphthyl)-7-aminosulfonyloxy-3,4-dihydro-benzo[e][1,3]oxazin-2-ones, 3-(cyclohexyl)-7-aminosulfonyloxy-3,4-dihydro-benzo[e][1,3]oxazin-2-ones, 3-(benzy)-7-aminosulfonyloxy-3,4-dihydro-benzo[e][1,3]oxazin-2-ones, 3-Cyclohexyl-7-hydroxy-3,4-dihydro-benzo[e][1,3]oxazin-2-one, 3-(4-Methoxyphenyl)-7-hydroxy-3,4-dihydro-benzo[e][1,3]oxazin-2-one, 3-(4-Hydroxcyclohexyl-7-hydroxy-3,4-dihydro-benzo[e][1,3]oxazin-2-one, 3-Phenyl-7-hydroxy-3,4-dihydro-benzo[e][1,3]oxazin-2-one, 3-(3-Hydroxyphenyl)-7-hydroxy-3,4-dihydro-benzo[e][1,3]oxazin-2-one, 3-(4-Hydroxyphenyl)-7-hydroxy-3,4-dihydro-benzo[e][1,3]oxazin-2-one, 3-(4-Aminosulfanyloxyphenyl)-7-hydroxy-3,4-dihydro-benzo[e][1,3]oxazin-2-one, 3-(4-(tert.butyl)(dimethyl)silyloxyphenyl)-7-hydroxy-3,4-dihydro-benzo[e][1,3]oxazin-2-one, 3-(6.7.9.10.12.13.15.16.18.19-decahydro-5,8,11,14,17,20-hexaoxybenzocyclooctadecen-2yl)-7-hydroxy-3,4-dihydro-benzo[e][1,3]oxazin-2-one, 3-(Phenylmethyl)-7-hydroxy-3,4-dihydro-benzo[e][1,3]oxazin-2-one, 3-(4-Trifluoromethyloxyphenyl)-7-hydroxy-3,4-dihydro-benzo[e][1,3]oxazin-2-one, 3-(4-Methoxyphenyl)-3,4-dihydro-benzo[e][1,3]oxazin-2-one, 3-(Biphenyl-4-yl)-3,4-dihydro-benzo[e][1,3]oxazin-2-one, 3-(Naphth-1-yl)-7-hydroxy-3,4-dihydro-benzo[e][1,3]oxazin-2-one, 3-(4-Bromophenyl))-3,4-dihydro-be[pi]zo[[theta]][1,3]oxazin-2-one, 3-(3-Aminosulfanyloxyphenyl)-7-aminosulfanyloxy-3,4-dihydro-benzo[8][1,3]oxazin-2-one, 3-Cyclohexyl-7-aminosulfanyloxy-3,4-dihydro-benzo[e][1,3]oxazin-2-one, 3-(4-Aminosulfanyloxyphenyl)-7-aminosulfanyloxy-3,4-dihydro-benzo[e][1,3]oxazin-2-one, 3-(4-Methoxyphenyl)-7-aminosulfanyloxy-3,4-dihydro-benzo[e][1,3]oxazin-2-one, 3-Phenyl-7-aminosulfanyloxy-3,4-dihydro-benzo[e][1,3]oxazin-2-one, 3-(4-Hydroxyphenyl)-7-aminosulfanyloxy-3,4-dihydro-benzo[e][1,3]oxazin-2-one, and 3-(Phenylmethyl)-7-aminosulfanyloxy-3,4-dihydro-benzo[e][1,3]oxazin-2-one, and a compound of formula:

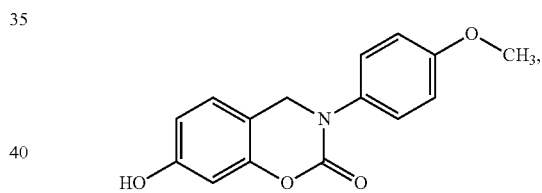

In one embodiment, said other MIF-inhibitor is a benzimidazolone analogue or derivative as described in WO2007/070961. Examples of such compounds include, but are not limited to,

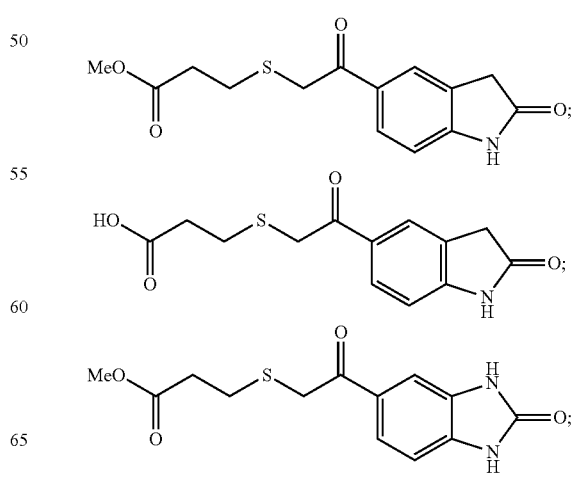

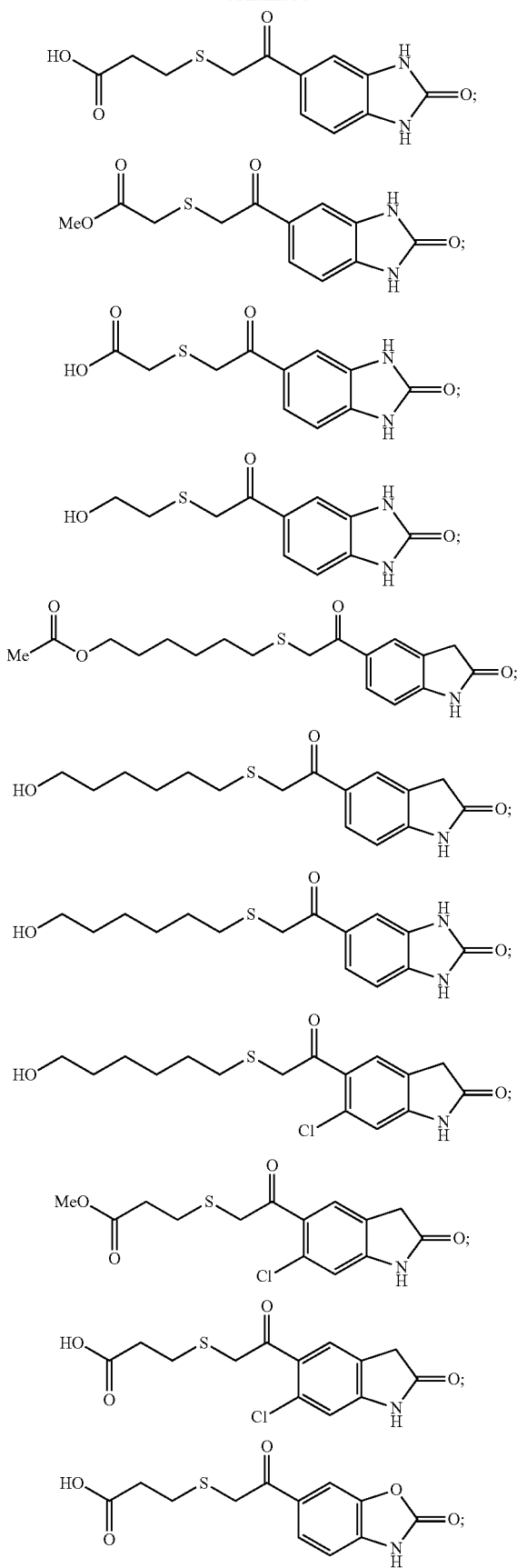
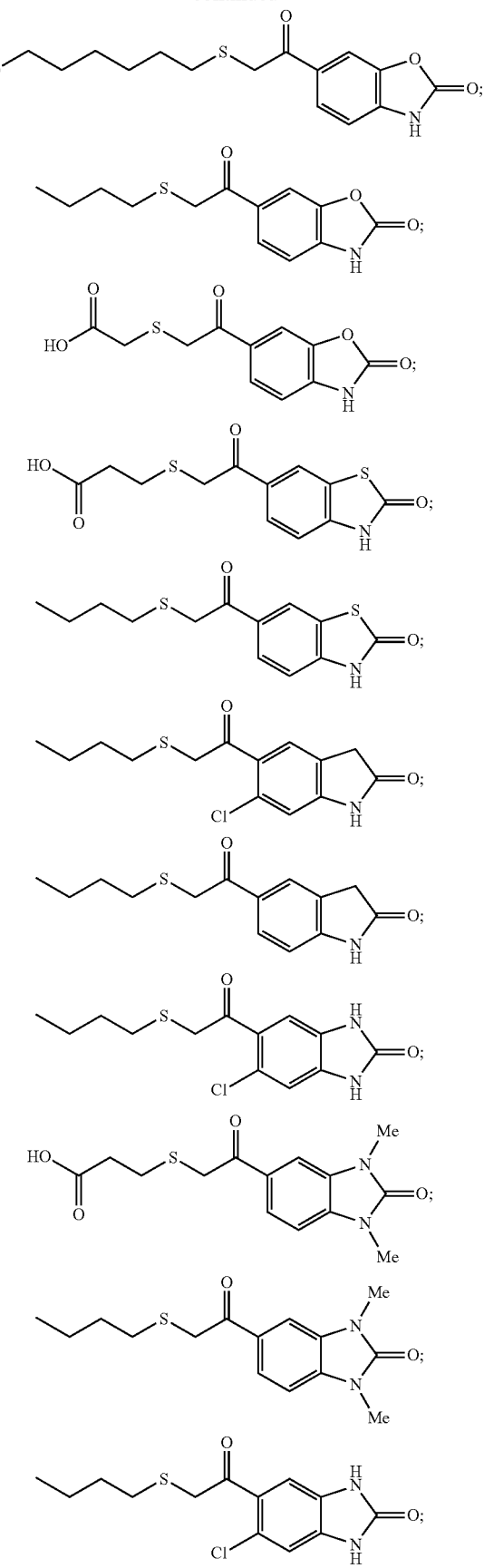

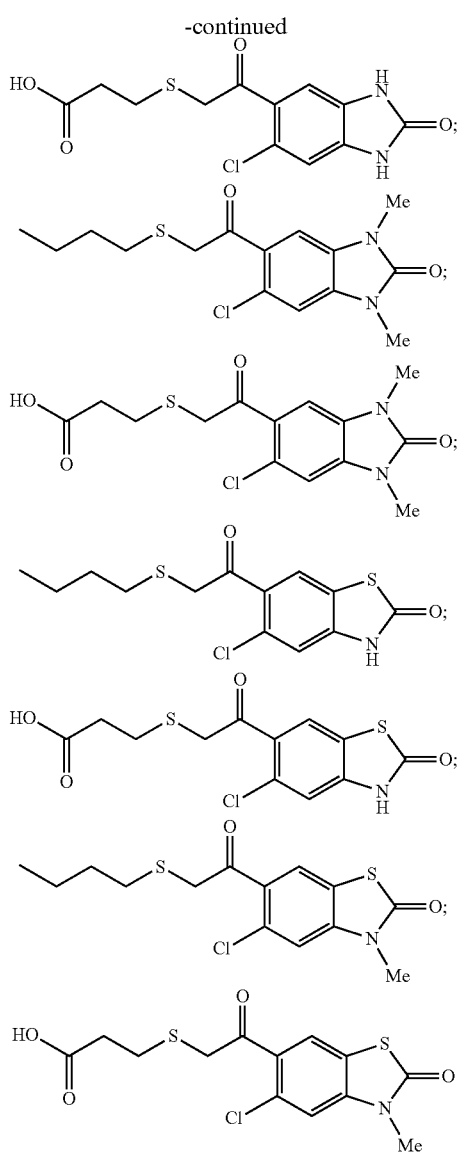

In one embodiment, said other MIF-inhibitor is a MIF-inhibitor described in US2012/039914, such as, for example, an antibody or fragment thereof which binds to an Ii polypeptide, or a MHC class II invariant chain (Ii) polypeptide or a fragment thereof which binds to MIF.

In one embodiment, said other MIF-inhibitor is an isoxazoline or isoxazoline-related compound described in US2013/225586. Examples of such isoxazoline or isoxazoline-related compounds include, but are not limited to, the compounds of the Table below (wherein Rx is a $(C_1-C_6)$ alkyl, $(C_2-C_6)$alkenyl, $(C_2-C_6)$alkynyl, phenyl, $(C_1-C_{10})$heteroaryl, $(C_1-C_{10})$heterocyclic or $(C_3-C_{10})$cycloalkyl substituent).

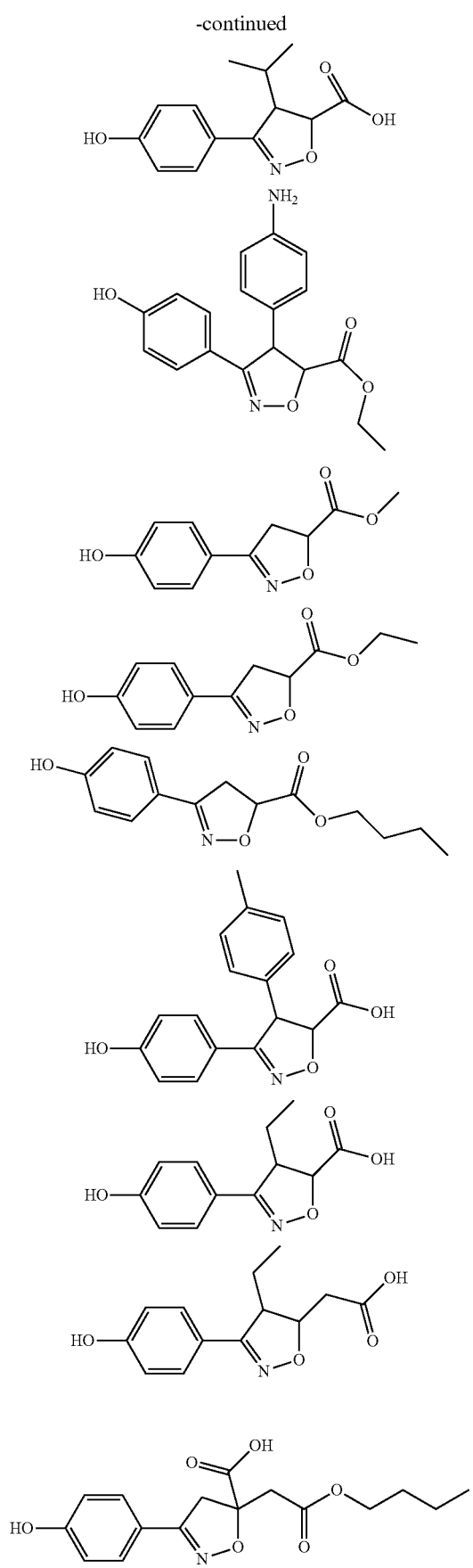

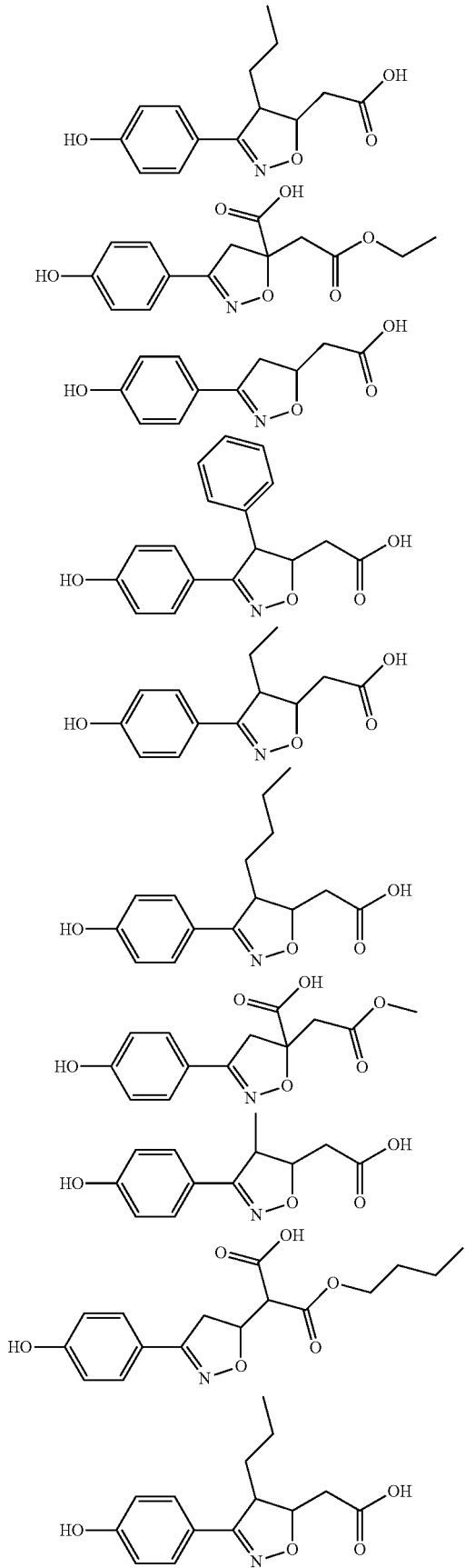
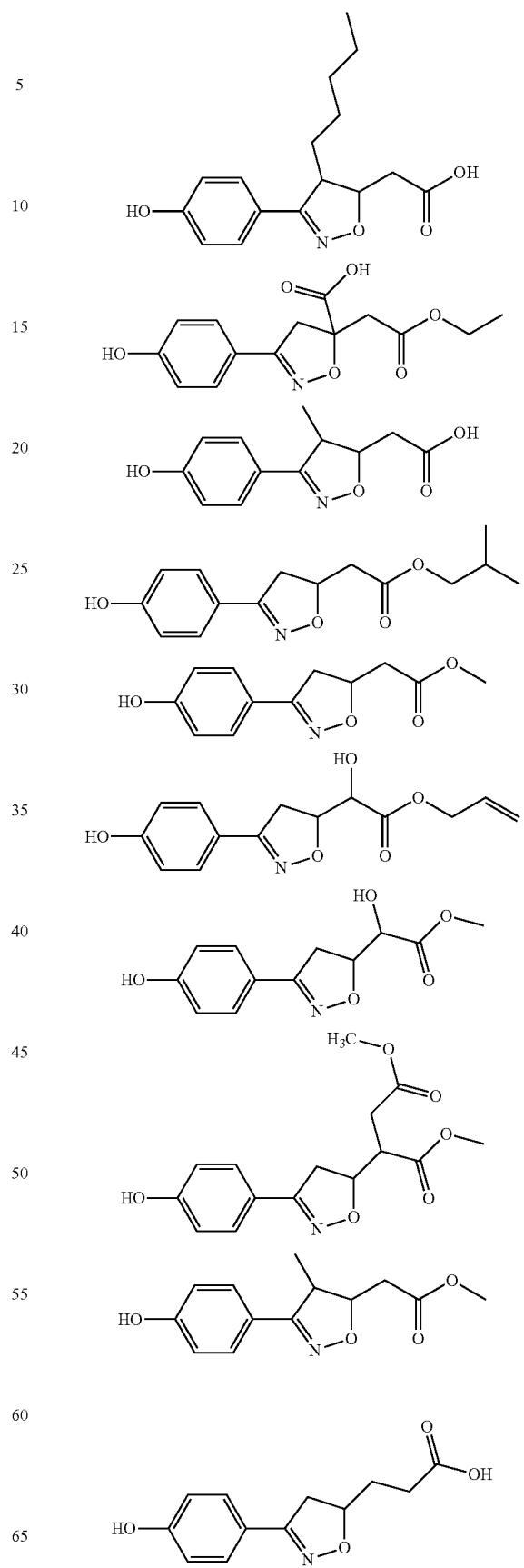

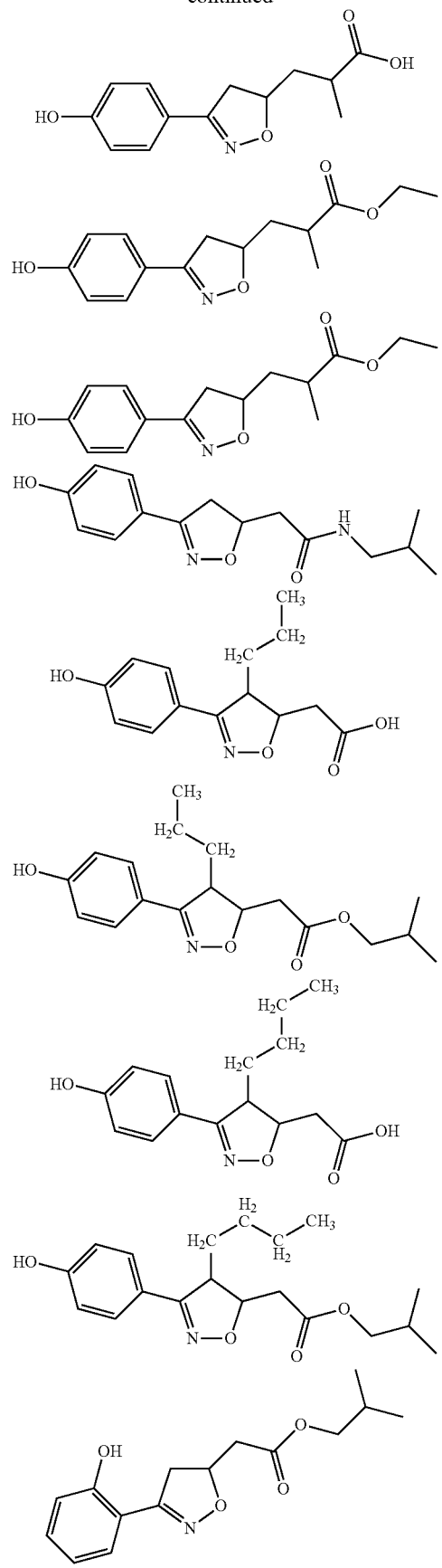
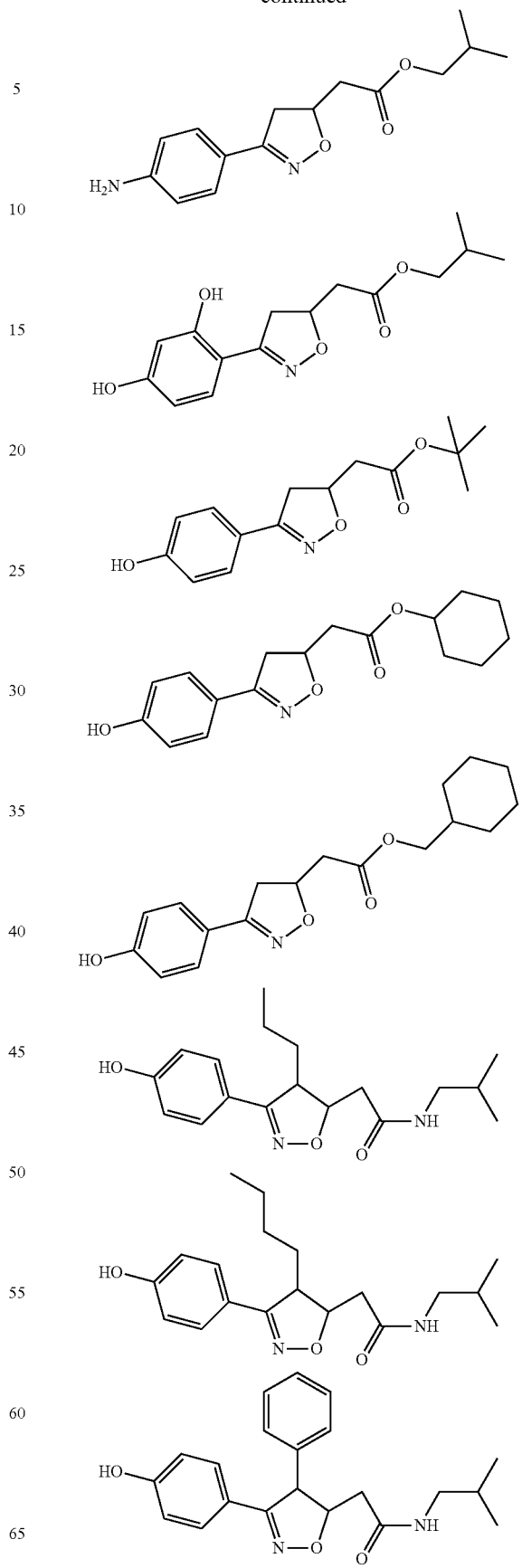

-continued
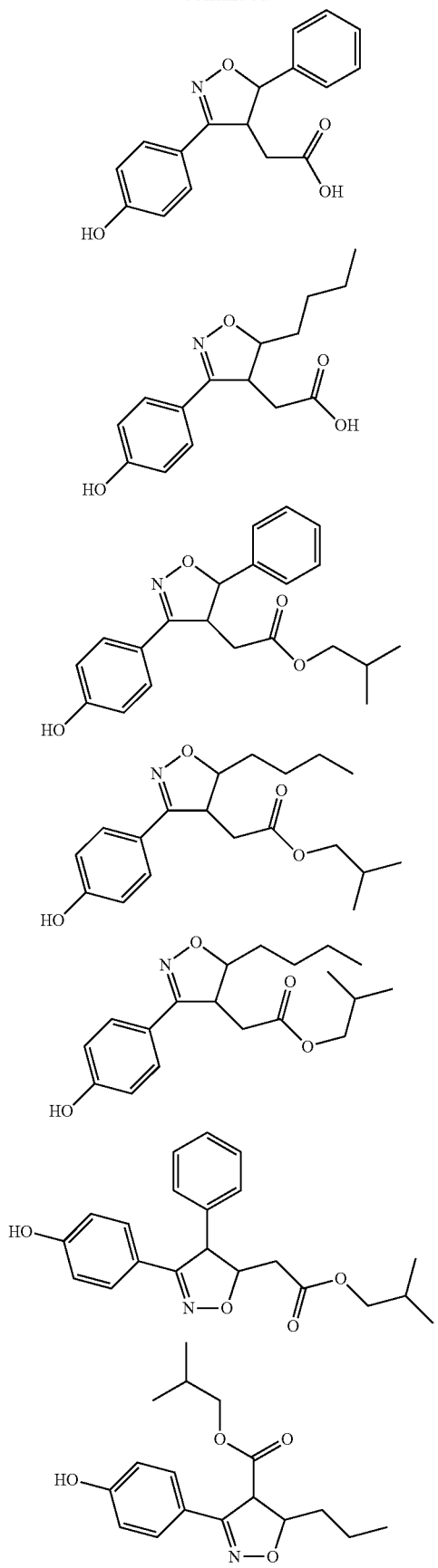
-continued
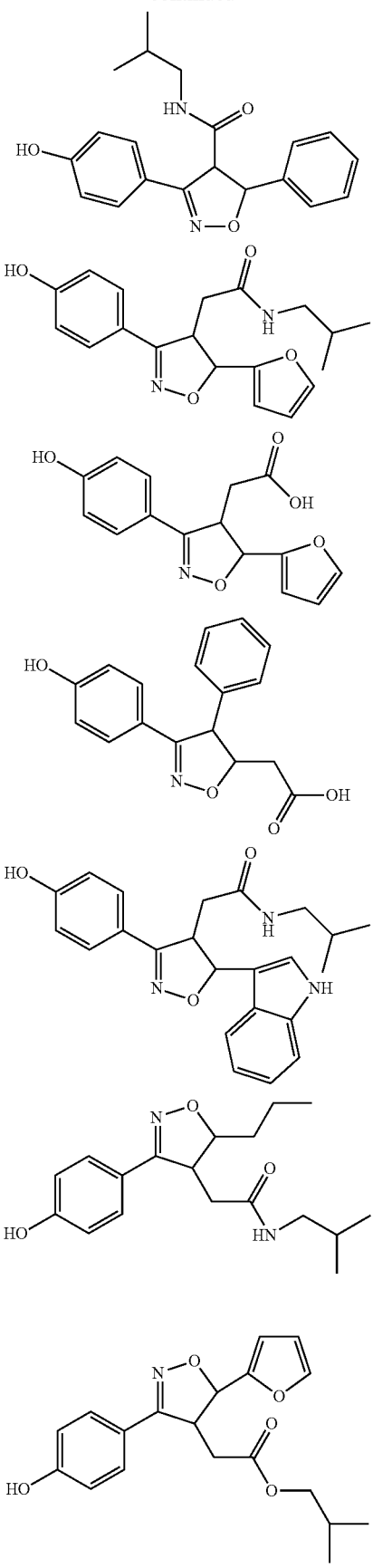

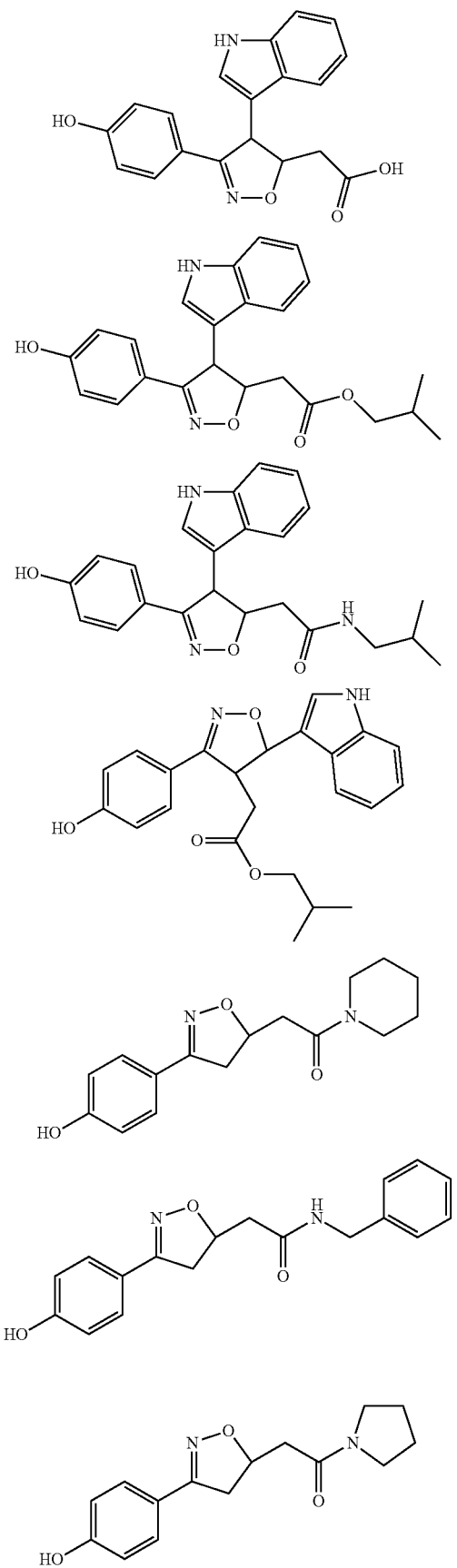
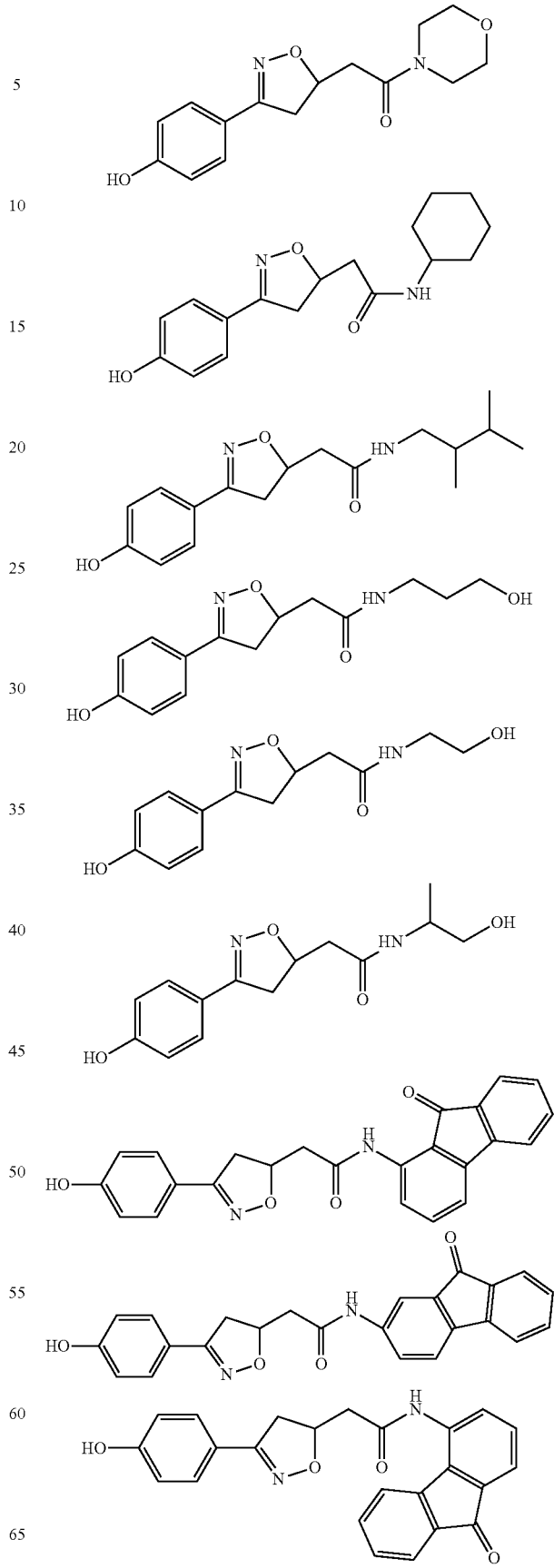

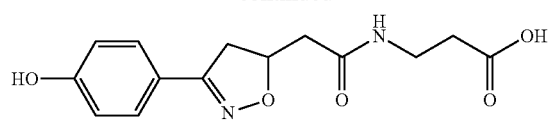
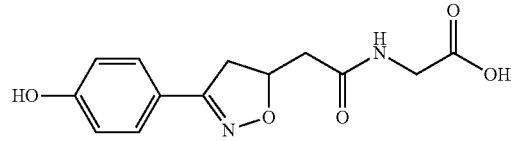
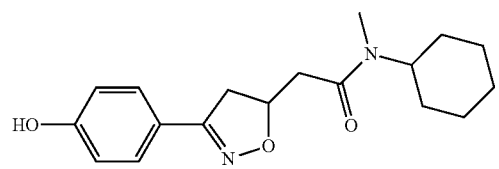
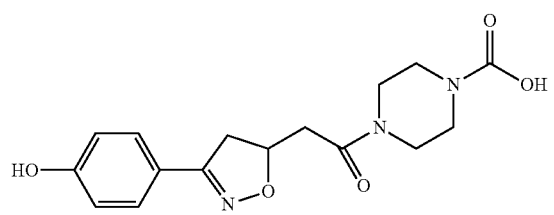
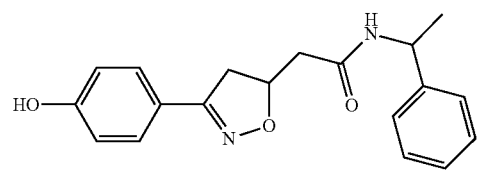
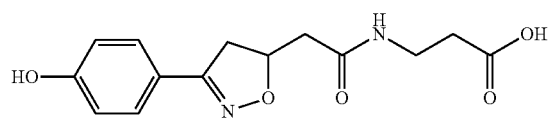
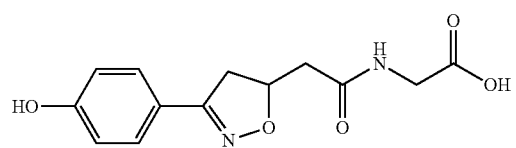
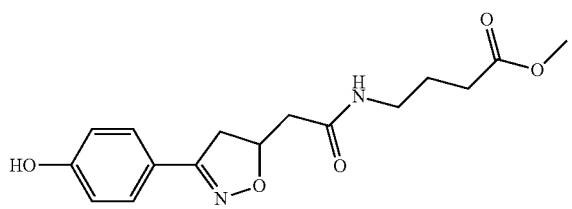
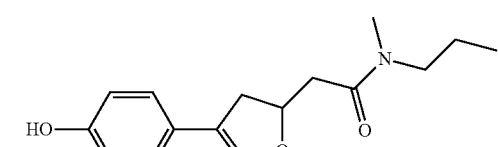
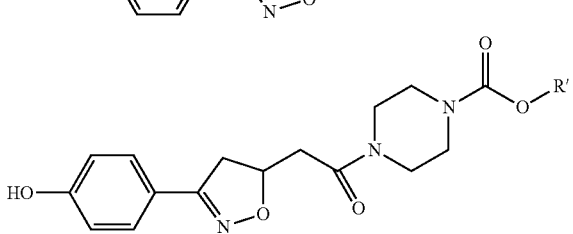
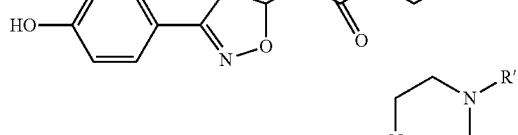
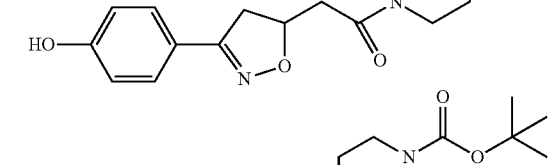
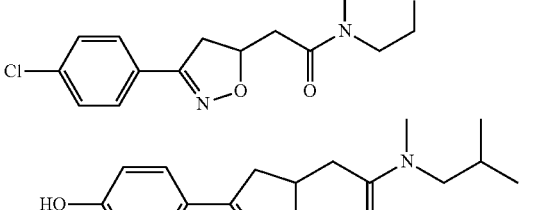
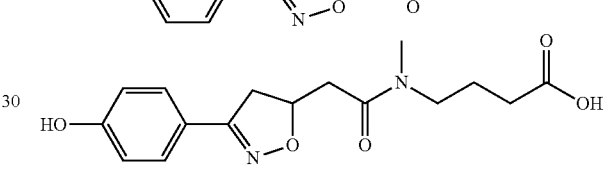
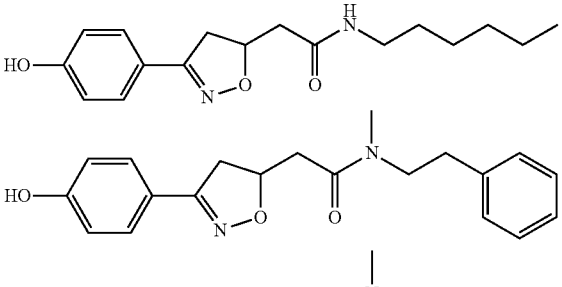
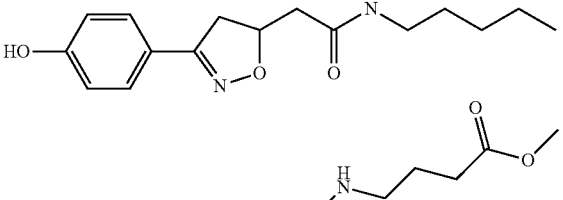
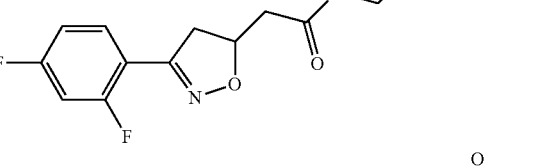
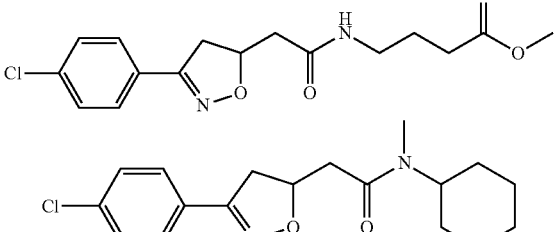

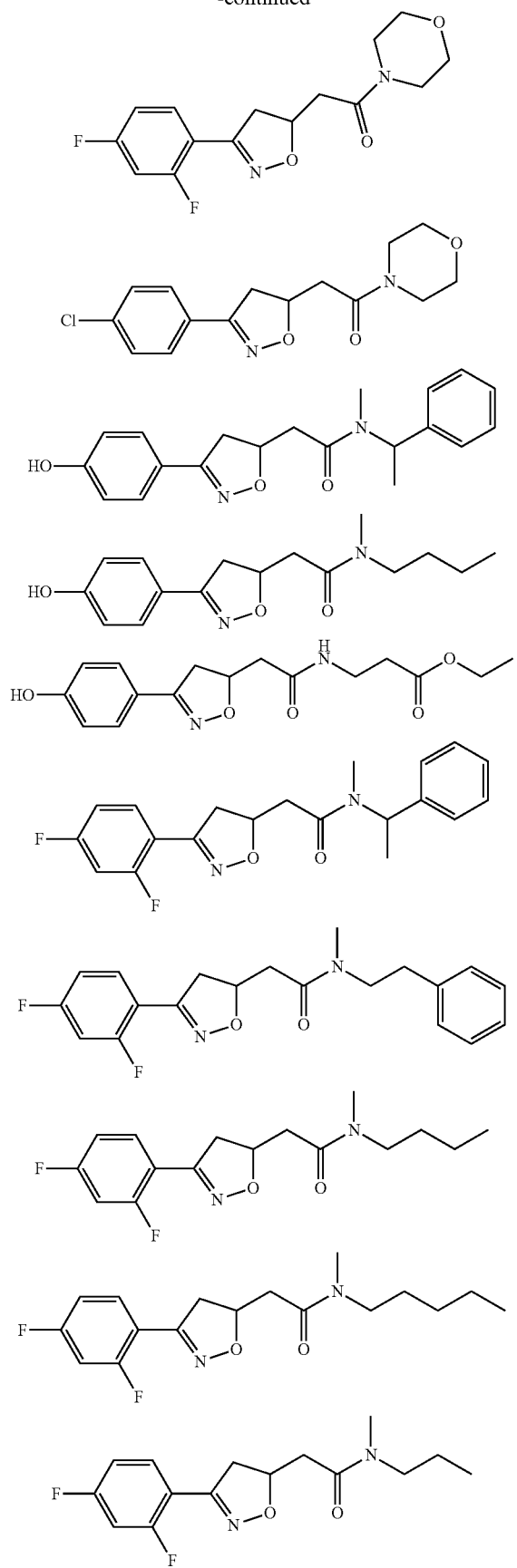
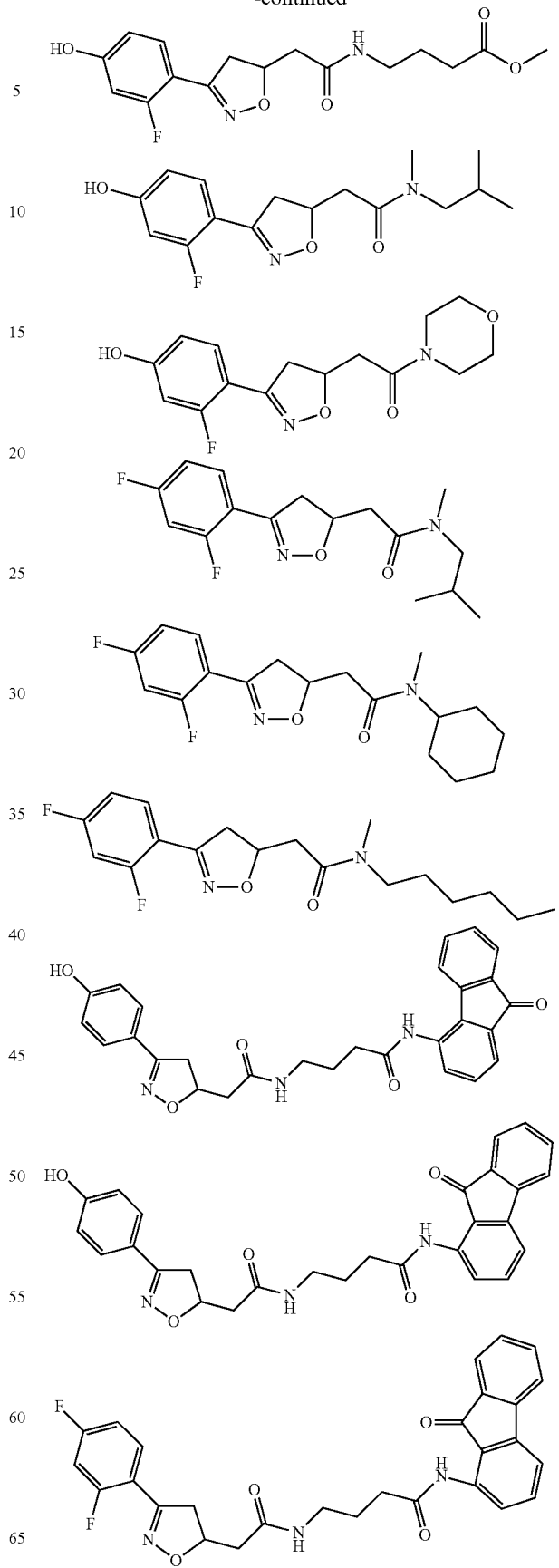

49
-continued
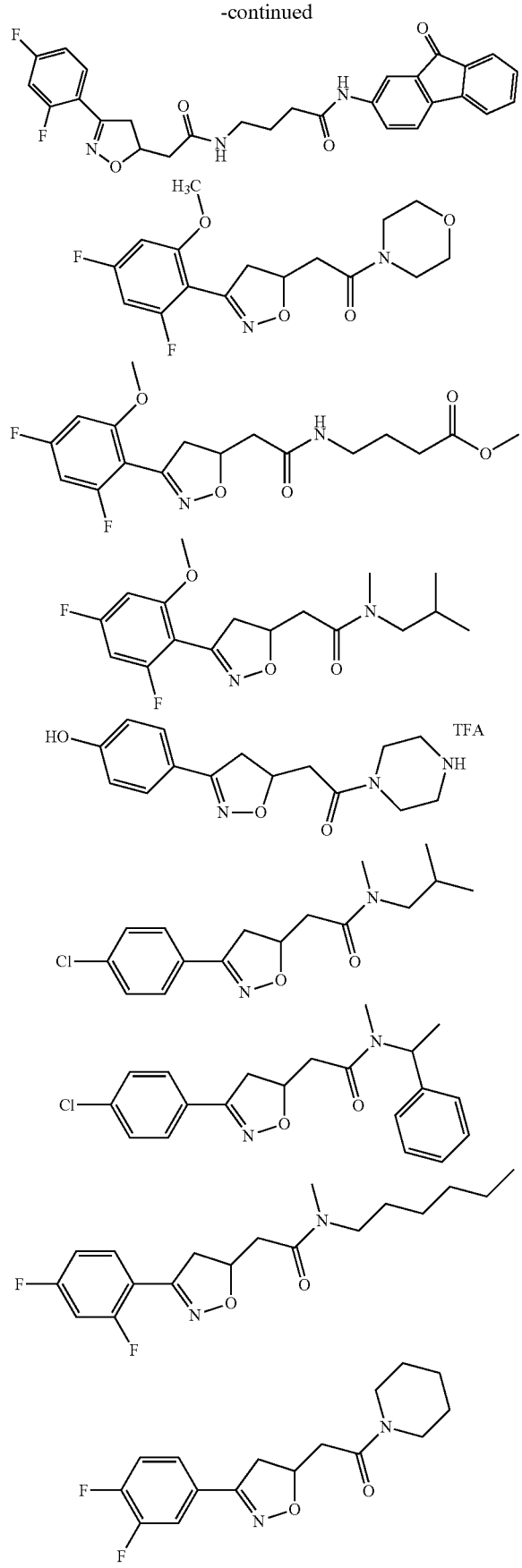
50
-continued
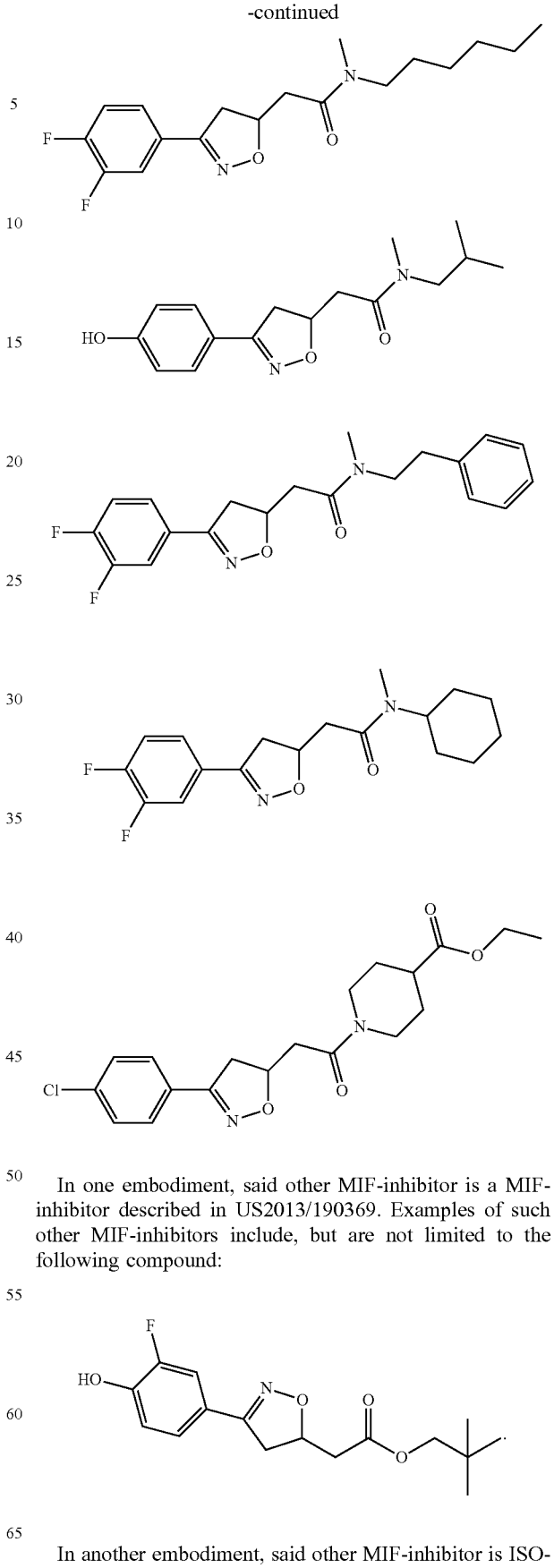
In one embodiment, said other MIF-inhibitor is a MIF-inhibitor described in US2013/190369. Examples of such other MIF-inhibitors include, but are not limited to the following compound:
In another embodiment, said other MIF-inhibitor is ISO-63 or ISO-60.

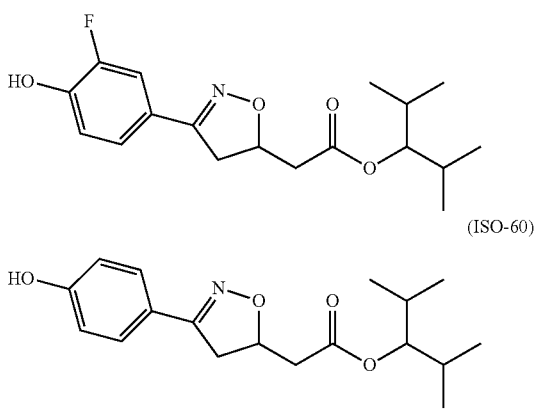

(ISO-63)

(ISO-60)

In one embodiment, the subject, preferably the patient is a mammal, preferably a human. In one embodiment, said subject is a female. In another embodiment, said subject is a male.

In one embodiment, the composition of the invention is perinatally administered to the subject. As used herein, the term "perinatally" refers to a few hours after birth, preferably 10, 8, 6, 5, 4, 3, 2 or 1 hour(s) after birth.

In one embodiment, the subject of the invention is a new born child. As used herein, the term "new born child" refers to a subject aged from 11; 12; 13; 14; 15; 16; 17; 18; 19; 20; 21; 22; 23 hour, 1; 2; 3; 4; 5; 6; 7; 8; 9; 10; 11; 12; 13; 14; 15; 16; 17; 18; 19; 20; 21; 22; 23; 24; 25; 26; 27; 28; 29; 30 days old.

In another embodiment, the subject of the invention is a young child. As used herein, the term "young child" refers to a subject from 0; 1; 2; 3; 4; 5; 6; 7; 8; 9; 10; 11 months old; 1 year old; 1 year and 3 months old; 1 year and 6 months old; 1 year and 9 months old; 2 years; 2 years and 3 months old; 2 years and 6 months old; 2 years and 9 months old; 3 years old.

In another embodiment, the subject of the invention is a child. As used herein, the term "child" refers to a subject aged from 4; 5; 6; 7; 8; 9; 10; 11; 12; 13; 14 years old.

In another embodiment, the subject of the invention is a teenager. As used herein, the term "teenager" refers to a subject aged from 15; 16; 17; 18; 19; 20 years old.

In another embodiment, the subject of the invention is an adult. As used herein, the term "adult" refers to a subject aged from any years above 20 years old.

In one embodiment, the subject is affected with, preferably is diagnosed with a pulmonary hypertension.

In another embodiment, the subject diagnosed with a pulmonary hypertension is already treated with other active agents as described herein to alleviate symptoms of PH.

In one embodiment, the subject diagnosed with a pulmonary hypertension is already treated with other active agents as described herein and does not respond adequately to these active agents (high pulmonary arterial pressure (such as, for example, pulmonary arterial pressure higher than about 20 mmHg, preferably higher than about 25 mmHg), or other adverse side effects that will be determined easily by the skilled artisan).

In another embodiment, the subject is at risk of developing a pulmonary hypertension.

In one embodiment of the invention, the subject presents a non-genetic predisposition to a pulmonary hypertension.

Risk factors for developing PH include, but are not limited to, connective tissue disease, systemic sclerosis, lung fibrosis, bronchiecstasis, hypoxia, hypoxemia, hypocapnia, chronic myoproliferative disorders, emphysema, diastolic left heart dysfunction, Sjögren syndrome, polymyositis, rheumatoid arthritis, collagen vascular disease (e.g. scleroderma), hereditary hemorrhagic telangiectasia, congenital shunts between the systemic and pulmonary circulation, portal hypertension, congenital heart disease, Eisenmenger syndrome, schistosomiasis, chronic hemolytic anemia, neurofibromatosis type 1, Recklinghausen disease, Gaucher disease, thyroid diseases, HIV infection, gene mutations (in the BMPR2, ACVRL1, ENG, CAV1, SMAD9, KCNK3 genes or other genes), drugs, and toxins increasing the risk of developing pulmonary hypertension.

Examples of drugs and toxins increasing the risk of developing pulmonary hypertension include, but are not limited to aminorex, fenfluramine and derivatives, toxic rapseed oil, cocaine, phenylpropanolamine, St. John's Wort, chemotherapeutic agents, selective serotonin reuptake inhibitor, amphetamines, L-tryptophan, cigarette smoking, tyrosine kinase inhibitors (for example dasatinib).

In one embodiment, the subject was prenatally exposed to antidepressants, maternal obesity, aminorex, fenfluramine and derivatives, toxic rapseed oil, cocaine, phenylpropanolamine, St. John's Wort, chemotherapeutic agents, selective serotonin reuptake inhibitor, amphetamines, L-tryptophan, cigarette smoking, tyrosine kinase inhibitors (for example dasatinib).

In another embodiment, the subject underwent a caesarian mode of delivery, a preterm delivery.

In one embodiment of the invention, the subject has a genetic or familial predisposition to a pulmonary hypertension. Examples of mutated genes associated with a pulmonary hypertension, preferably a pulmonary arterial hypertension include: BMPR2 gene, Activin receptor-like kinase type 1 (ACVRL1 or ALK1) gene, Endoglin (ENG) gene, SMAD9 gene, KCNK3 gene, Caveolin-1 (CAV1) gene, and other unknown genes.

The present invention also relates to a method for treating pulmonary hypertension in a subject in need thereof, comprising the administration of a therapeutically effective amount of a compound of general Formula I, or of the composition, pharmaceutical composition or medicament of the invention.

The present invention also relates to a method for preventing, reducing or alleviating the symptoms associated with pulmonary hypertension in a subject in need thereof, comprising the administration of a therapeutically effective amount of a compound of general Formula I, or of the composition, pharmaceutical composition or medicament of the invention.

In one embodiment, the method of the invention relates to an acute treatment of PH. In another embodiment, the method of the invention relates to a chronic treatment of PH. In another embodiment, the method of the invention relates to an acute treatment subsequently to a chronic treatment of PH. In one embodiment, the method of the invention relates to the treatment of an acute form of PH. In another embodiment, the method of the invention relates to the treatment of a chronic form of PH. In another embodiment, the method of the invention relates to the treatment of an acute form of PH subsequently to the treatment of a chronic form of PH.

As shown in the Examples, the Inventors herein demonstrate that the compound for use of the invention inhibits selectively the MIF CD74 axis, preferably the MIF CD74 pathway.

CD74 (invariant chain, Ii) is a non-polymorphic transmembrane glycoprotein that exists in different isoforms and plays a major role in regulating the trafficking of major histocompatibility complex (MHC) class II proteins in antigen-presenting cells (Leng L et al. 2003 J Exp Med 197 (11): 1467-1476). However, CD74 can also be expressed in the absence of the MHC class II protein (2-5%) and has recently been reported to be a high-affinity binding protein for the pro-inflammatory cytokine macrophage migration inhibitory factor (MIF), providing evidence for a role in signal transduction pathways (Leng L et al. 2003 J Exp Med 197 (11): 1467-1476). The lung is a major source of MIF, which is released upon stimulation by stress, endotoxins, inflammatory and immune stimuli and plays a pivotal upstream role in the inflammatory cascade. Stimulation of CD74 initiates a signaling cascade through the sustained and transient activation of the mitogen-activated protein kinases (MAPKs) extracellular signal-regulated kinase (ERK)1 and ERK2, Src, protein kinase B (AKT) and nuclear factor (NF)-κB, leading to leukocytic integrin activation, cell proliferation, and survival and induction of pro-inflammatory gene expression (Lue H et al. Oncogene 2007 26(35): 5046-59; Gore Y et al. J Biol Chem. 2008 Feb. 1; 283(5): 2784-92; Takahashi K et al. Respir Res. 2009; 10:33).

The present invention thus also relates to a method for treating pulmonary hypertension, preferably pulmonary arterial hypertension, comprising administering a compound of general Formula I, thereby inhibiting the interaction between MIF and CD74 in a subject in need thereof.

The present invention thus also relates to a method for treating pulmonary hypertension, preferably pulmonary arterial hypertension, comprising administering a compound of general Formula I, thereby inhibiting the axis and/or signalling pathway downstream MIF and its receptors such as CD74 or CXCRs in a subject in need thereof.

The present invention also relates to a method for treating pulmonary hypertension, preferably pulmonary arterial hypertension, comprising administering a compound of general Formula I, thereby inhibiting the inflammation within the lungs in a subject in need thereof.

The present invention also relates to a method for treating pulmonary hypertension, preferably pulmonary arterial hypertension, comprising administering a compound of general Formula I, thereby inhibiting the proliferation of pulmonary vascular cells within blood vessels connected to or within the lungs in a subject in need thereof.

The present invention also relates to a method for treating pulmonary hypertension, preferably pulmonary arterial hypertension, comprising administering a compound of general Formula I, thereby inhibiting lung inflammation/autoimmune mechanisms in a subject in need thereof.

The present invention also relates to a method for inhibiting the inflammation and/or dysimmunity within the lungs, comprising administering a compound of general Formula I, in a subject in need thereof.

The present invention also relates to a method for inhibiting the pulmonary vascular cell proliferation/survival, comprising administering a compound of general Formula I, in a subject in need thereof.

EXAMPLES

Figure 1:
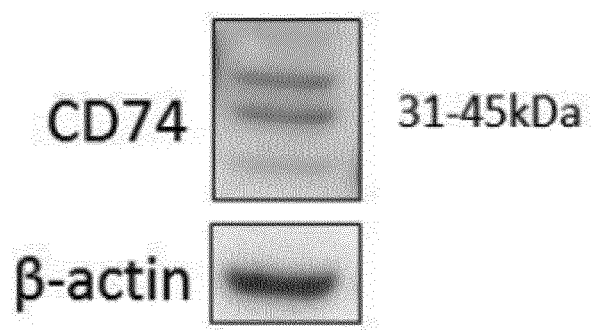
FIG. 1 is Western blot showing MIF receptor expression in DU-145 and iPAH EC cell lines.
Figure 1:
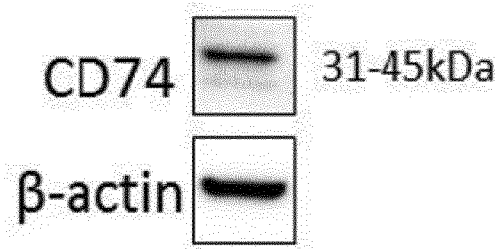

The present invention is further illustrated by the following examples.

Chemistry Examples

Material

Tetrahydrofuran was distilled from sodium and benzophenone. Methanol was distilled from magnesium turnings. Analytical TLC was performed on precoated Merck 60 $F_{254}$ glass plates and visualized by exposure to ultraviolet light (254 nm) or by using solution of 20% phosphomolybdic acid in EtOH or vanillin/sulfurinic acid/acetic acid in EtOH. IR spectra were measured on a Bruker Vector 22 spectrophotometer (neat, $cm^{-1}$). $^{1}H$ and $^{13}C$ NMR spectra were recorded in $CDCl_3$ or DMSO-$d_6$ on a Bruker Avance 300 and chemical shifts are reported in ppm. The following abbreviations for multiplicity are used: m (multiplet), s (singlet), br s (broad singlet), d (doublet), t (triplet), dd (doublet of doublet), td (triplet of doublet), q (quadruplet).

General Method of Synthesis

N-(methyl aryl)-benzoxazol-2-thiones were synthesized following a three-step synthetic pathway represented in the scheme below.

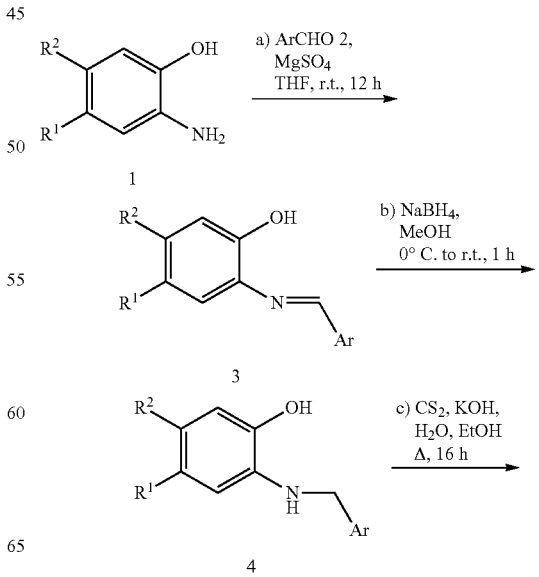

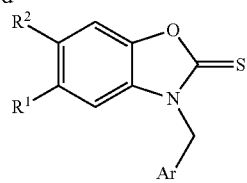

The synthesis begins by condensation of 2-aminophenol derivative 1 with various aldehydes 2. Subsequent reduction of resulting imine 3 with sodium borohydride, followed by cyclization of the resulting amino alcohol 4 with carbon disulfide leads to the N-(methyl aryl)-benzoxazol-2-thione 5 in good overall yield (60-90%). This three step sequence requires no purification of intermediate 3 and 4. A final purification by precipitation of 5 gives pure compounds.

The benzaldehyde derivative 2 (1 eq.) is added to a stirred mixture of aminophenol derivative 1 (1 eq.) and anhydrous MgSO$_4$ (4 eq.) in THF at room temperature. After 12 h of stirring, the mixture is filtered and the filtrate is concentrated to give the crude imine 3, which is used without further purification. Sodium borohydride (1.3 eq.) is added portionwise to a solution of the crude imine 3 in THF at 0° C. After the completion of the addition, the reaction mixture is maintained at room temperature for 30 min and then concentrated in vacuo. The reaction mixture is redissolved in EtOAc and washed with H$_2$O (×2). The combined aqueous extracts are extracted with EtOAc (×3). The combined organic phases were washed with brine (×2), dried over Na$_2$SO$_4$ and concentrated to give the crude amino alcohol 4. KOH (0.5 eq.) and carbon disulfide (4 eq.) are added to a solution of the crude amino alcohol 4 in a mixture of EtOH/H$_2$O. The reaction mixture is heated at reflux for 16 h, then cooled to 0° C. Water is added to precipitate N-(methyl aryl)-benzoxazol-2-thione 5, which is recovered by filtration.

Product Characterization

Compound 1:

$^{13}$C NMR (75 MHz, DMSO-d$_6$): 179.9; 157.6; 144.7; 135.9; 135.0; 131.4; 129.8; 125.1; 119.0; 115.0; 114.0; 110.9; 109.9; 48.1; 20.9 Yield: 86%.

Compound 2:

$^{13}$C NMR (75 MHz, DMSO-d$_6$): 181.2; 156.9; 145.3; 134.9; 132.0; 129.5; 128.9; 124.8; 122.0; 120.8; 110.6; 110.5; 109.7; 55.3; 44.0; 21.5.

Compound 3:

$^{13}$C NMR (75 MHz, DMSO-d$_6$): 181.1; 145.4; 135.2; 134.0; 131.7; 129.0 (2C); 128.3; 127.6 (2C); 125.0; 110.2; 109.9; 49.4; 21.5.

Compound 4:

$^{1}$H NMR (300 MHz, DMSO-d$_6$): 9.92 (s, 1H); 7.45 (d, J=8.4 Hz, 1H); 7.23 (s, 1H); 7.14-7.08 (m, 2H); 6.99 (dd, J=2.1, 8.4 Hz, 1H); 6.89-6.83 (m, 1H); 5.34 (s, 2H); 2.35 (s, 3H).

Compound 5:

$^{1}$H NMR (300 MHz, CDCl$_3$): 7.54 (dq, J=0.6, 8.4 Hz, 1H); 7.44 (d, J=8.4 Hz, 1H); 7.19-7.18 (m, 1H); 7.11-7.03 (m, 2H); 6.92-6.87 (m, 1H); 5.36 (s, 2H).

Biological Examples

Materials and Methods

Chemical Compounds

In the following examples, the following chemical compounds are used:

| Compound | Formula |
|---|---|
| ISO-1 (control) | |
| M3 (compound 1 of the invention) | |
| M41 (M3 "C=O" isostere) | |
| compound 2 of the invention | |
| compound 3 of the invention | |

| Compound | Formula |
| --- | --- |
| compound 4 of the invention | 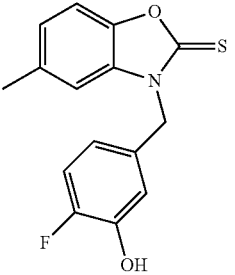 [SMILES: Cc1ccc2oc(=S)n(Cc3ccc(F)c(O)c3)c2c1] |
| compound 5 of the invention | 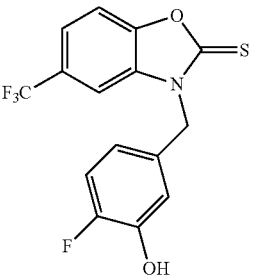 [SMILES: Oc1cc(Cn2c(=S)oc3ccc(C(F)(F)F)cc32)ccc1F] |

MIF Tautomerase Assay Using 4-Hydroxyphenylpyruvate (4-HPP)

Tautomerase activity was assessed using 4-hydroxyphenylpyruvate (4-HPP) as substrate. 4-HPP was dissolved in 50 mM ammonium acetate at pH 6.0, allowed to equilibrate to room temperature and stored at −20° C. 300 ng/mL of recombinant human MIF (rhMIF; RayBiotech, Le Perray en Yvelines, France) and tested compounds were pre-incubated at room temperature for 15 min. Tautomerase activity was assessed at room temperature, by adding 4-HHP to a 96-well plate containing 0.435 M boric acid at pH 6.6 and rhMIF with or without (positive control) tested compounds (1 nM), and by measuring the increase in absorbance at 320 nm over 10-360 s using the 2103 EnVision™ Multilabel Plate Readers (PerkinElmer, Villebon-sur-Yvette, France). Compounds were tested at 1 nM. The assay was replicated 3 to 6 times independently.

Isolation, Culture of Human Pulmonary Endothelial Cells (P-ECs)

P-ECs were isolated and cultured from lung specimens of patients with idiopathic pulmonary arterial hypertension (iPAH) as previously described (Tu et al., Am J Respir Cell Mol Biol. 2012). The isolated P-ECs were strongly positive for acetylated low-density lipoprotein coupled to Alexa 488 (Alexa488-Ac-LDL), von Willebrand factor (vWF), CD31, and for *Ulex europaeus* agglutinin-1 (UEA-1) and negative for alpha-smooth muscle actin (α-SMA). DU-145 cell lines and iPAH ECs were grown in MCDB131 medium (Fisher, Illkirch Cedex, France) supplemented with 10% fetal calf serum (FCS), penicillin-streptomycin solution, glutamine, HEPES and amphotericine.

Evaluation of the Compounds of the Invention on Cell Proliferation and Survival: Methyl Tetrazolium (MTT) Assay To determine the impact of the compounds of the invention on the proliferation and the survival of DU-145 cell line and iPAH P-ECs, the methyl tetrazolium (MTT) assay was performed. To this aim, cells were plated in a 96-well plate and cultured in MCDB131 medium (Fisher, Illkirch Cedex, France) supplemented with 10% fetal calf serum (FCS) for 24 h. DU-145 and iPAH ECs monolayers were then washed and 50 or 100 μM of tested compounds were added with 0% (for cell survival assessment) or 10% (for cell proliferation assessment) of FCS for 24 h. Then, cells were incubated with 5 mg/mL of MTT for 6 h of incubation. At the end of the incubation time, medium was removed, dimethylsulfoxide (DMSO) was added in each well and absorbance was recorded at 590 nm using the microplate spectrophotometer system EnVision (PerkinElmer, Waltam, USA).

Rodent Model of Pulmonary Hypertension

Animal studies were approved by the administrative panel on animal care at the Univ. Paris-Sud, Le Plessis-Robinson, France. Young male Wistar rats (100 g, Janvier Labs, France) were studied 3 weeks after a single subcutaneous injection of monocrotaline (60 mg/kg) (Sigma-Aldrich, Saint-Quentin Fallavier, France), or vehicle. One week after a single subcutaneous injection of monocrotaline (MCT), rats were randomly divided into several groups and treated for 2 weeks with (example 3) daily intraperitoneal injections of ISO-1, compound 1 of the invention (M3), M41, or vehicle (vehicle A: 50% (v/v) DMSO (Dimethyl sulfoxide) in normal saline for i.v. administrations) at a dose of 10 mg·kg$^{-1}$·day$^{-1}$; or (example 4) daily per os administration of compounds of the invention, or vehicle (vehicle B: 33% DMSO, 45% propylene glycol, 21% saline) at a dose of 30 mg·kg$^{-1}$·day$^{-1}$.

Animals were anesthetized with isoflurane. A polyvinyl catheter was introduced into the right jugular vein and pushed through the right ventricle into the pulmonary artery. Cardiac output in rat was measured using the thermodilution method. After measurement of hemodynamic parameters, the thorax was opened and the left lung immediately removed and frozen. The right lung was fixed in the distended state with formalin buffer. The right ventricular hypertrophy (RVH) index and the percentage of muscularized vessels were determined as previously described (Guignabert C 2009 J Faseb 23 (12): 4135-4147).

Statistical Analyses

Statistical significance was tested using the nonparametric Mann-Whitney test or the nonparametric Kruskal-Wallis test with post-hoc Dunn's test.

Results

Example 1: MIF Tautomerase Assay

The compound 1 (M3) of the present invention was tested and compared to its "C═O" isostere (M41). Compounds 2-5 of the present invention were also tested. Results are also compared to prototypical MIF inhibitor ISO-1.

Results are presented in Table 1 below, and represent the percentage of MIF tautomerase activity inhibition as compared to the positive control with recombinant human MIF alone.

TABLE 1

| \multicolumn{2}{c}{tested compound} | tautomerase activity |
|---|---|---|
| Name | Structure | inhibition (%) |
| ISO-1 | [structure: 3-(4-hydroxyphenyl)-4,5-dihydroisoxazol-5-yl acetic acid methyl ester] | 21 |
| M3 (Compound 1 of the invention) | [structure: 5-methyl-3-(3-hydroxybenzyl)benzoxazole-2-thione] | 41 |
| M41 (M3 isostere) | [structure: 5-methyl-3-(3-hydroxybenzyl)benzoxazole-2-thione isostere] | 29 |
| Compound 2 | [structure: 5-methyl-3-(2-methoxybenzyl)benzoxazole-2-thione] | 36 |
| Compound 3 | [structure: 5-methyl-3-benzylbenzoxazole-2-thione] | 35 |
| Compound 4 | [structure: 5-methyl-3-(3-fluoro-4-hydroxybenzyl)benzoxazole-2-thione] | 39 |

TABLE 1-continued

Efficacies on tautomerase activity using 4-HPP

| tested compound | | tautomerase activity |
|---|---|---|
| Name | Structure | inhibition (%) |
| Compound 5 | [structure: 5-trifluoromethyl-3-(4-fluoro-3-hydroxybenzyl)benzoxazole-2-thione, F$_3$C-substituted benzoxazole with N-CH$_2$-phenyl(F)(OH) and C=S] | 43 |

The compound 1 of the invention shows a good inhibitory effect against the MIF tautomerase activity as compared to its corresponding benzoxazol-2-one analogue (M41).

Besides, all tested compounds of the invention exhibit a higher inhibitory effect against the MIF tautomerase activity as compared to the prototypical MIF inhibitor ISO-1.

Example 2: Cell Proliferation and Survival

The effect of the compounds of the invention on cell proliferation and cell survival was tested for DU-145 and iPAH P-EC cell lines. These cell lines are known to express MIF receptors (including CD74), which upon linkage with MIF ligands induce signalization for cell proliferation and survival.

Western blot analyses were conducted on cell lysates, confirming the protein expression of CD74 by the two cell lines (FIG. 1).

Figure 2A:
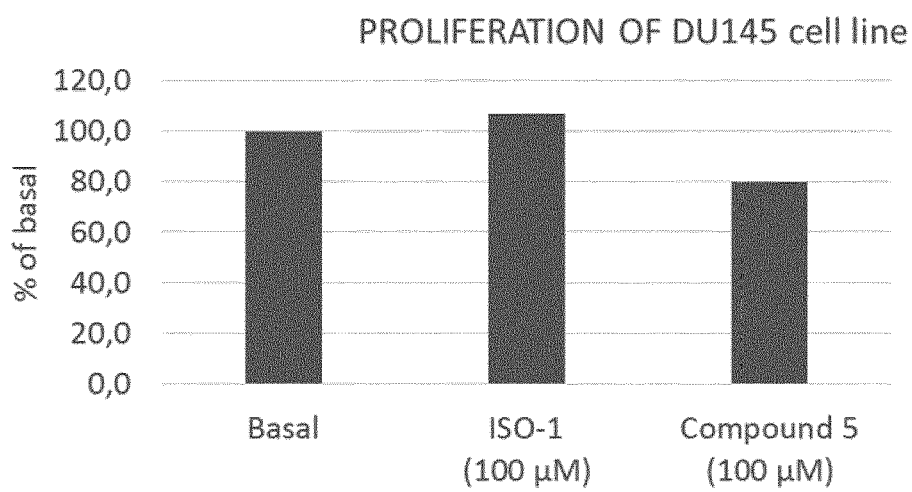
FIGS. 2A and 2B are histograms showing cell proliferation in presence of compound 5 of the invention in DU-145 and iPAH EC cell lines.
Figure 2B:
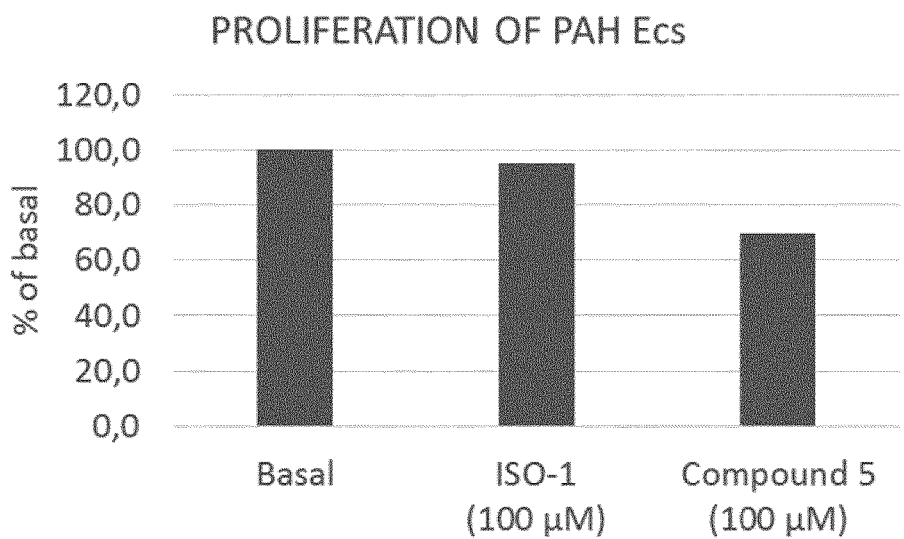

A MTT assay was then conducted to determine cell proliferation in presence of compound no 5 according to the invention. As shown FIGS. 2A and 2B, compound no 5 enables to inhibit significantly cell proliferation of the two cell lines. The effect is significantly superior compared to ISO-1 ($p<0.05$).

Figure 3A:
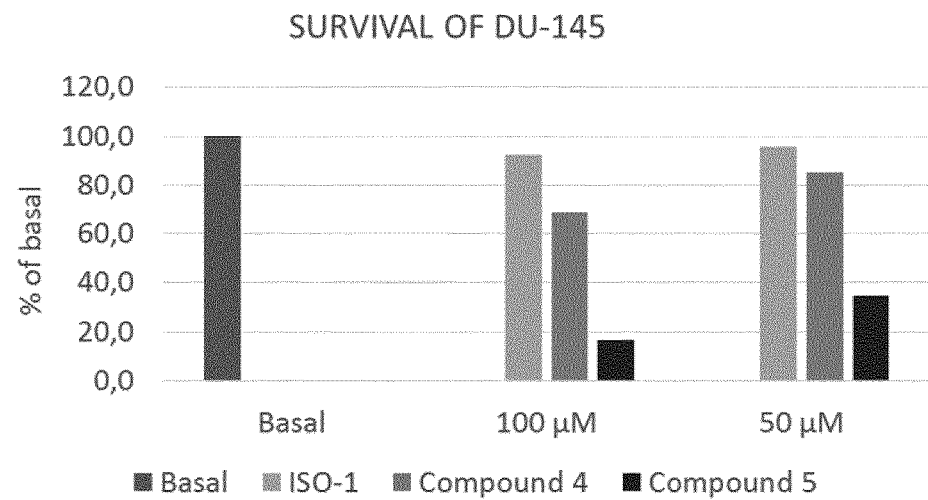
FIGS. 3A and 3B are histograms showing cell survival in presence of compounds 4 or 5 of the invention in DU-145 and iPAH EC cell lines.
Figure 3B:
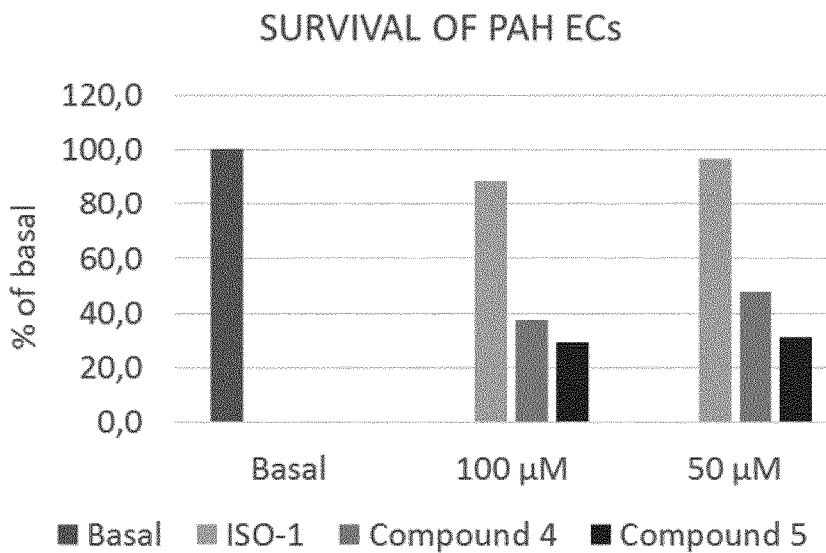

A MTT assay was also conducted to determine cell survival in presence of compounds no 4 or 5 according to the invention. As shown FIGS. 3A and 3B, compounds no 4 or 5 enable to decrease significantly cell survival in the two cell lines, at 100 μM and 50 μM. The effect is significantly superior compared to ISO-1 ($p<0.05$).

Example 3: Efficacies of Treatment with the Compound 1 of the Invention (M3) on the Progression of MCT-Induced PAH Efficacies of compound 1 of the invention (M3), prototypical MIF inhibitor ISO-1 and M41 (isosteres of M3) were tested on the development of experimental PH.

Figure 4:
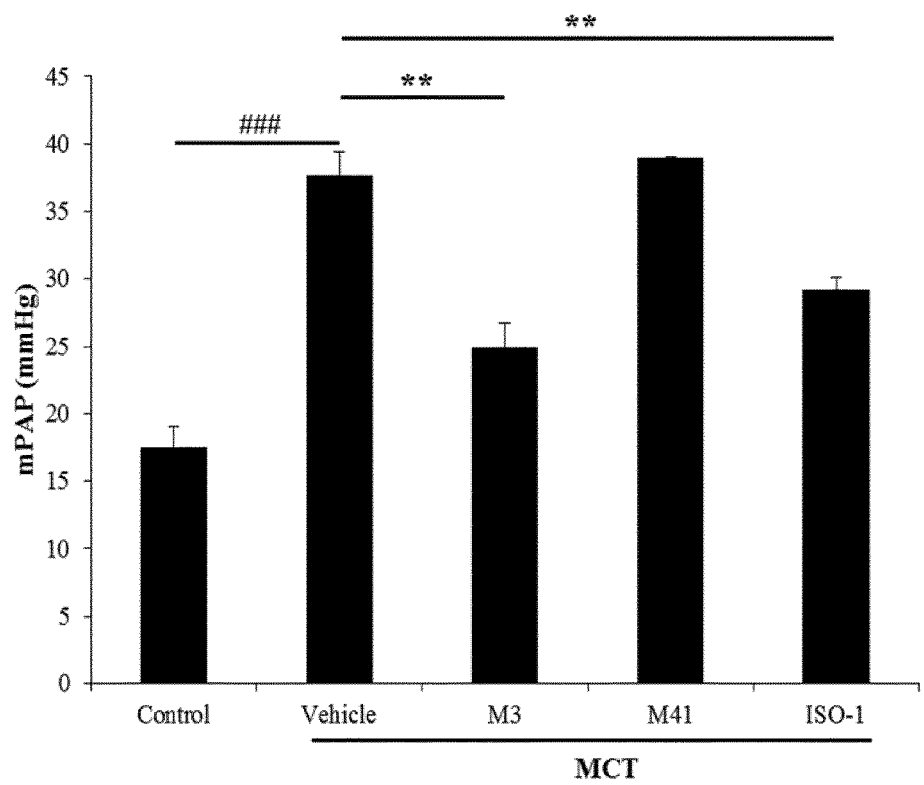
FIG. 4 is a histogram showing the effect of compound 1 of the invention on the mean pulmonary arterial pressure (mPAP) of a rat model of PH. ### p-value<0.001 compared with vehicle-injected rats with the t-test. ** p-value<0.01 compared with MCT-injected rats with the t-test.

Daily treatment for 2 weeks with compound 1 (M3) or M41 started one week after a subcutaneous MCT injection substantially attenuates the degree of established PH (FIG. 4). On day 21, in MCT-injected rats treated with vehicle A, a marked increase in mean pulmonary arterial pressure (mPAP), right ventricular hypertrophy (RVH) and numbers of muscularized distal pulmonary arteries were found compared with controls (FIG. 4). However, there was a substantial reduction in values of mPAP between monocrotaline-injected rats treated with either compound 1 (M3) or ISO-1 at a dose of 10 mg/kg as compared to monocrotaline-injected rats treated with vehicle A (FIG. 4). Interestingly, we found that compound 1 (M3) had higher beneficial effects in mPAP (at the same dose, 10 mg/kg) as compared to MCT-injected rats treated with ISO-1 ($p=0.0855$). In addition, we noted a high mortality rate in the group of MCT-injected rats treated with M41 (5/6).

These results thus strongly support the use of the compound of the invention for treating pulmonary hypertension.

Example 4: Efficacies of Treatment with Compounds 4 or 5 of the Invention on the Progression of MCT-Induced Pulmonary Hypertension Efficacies of compounds 4 and 5 of the invention were tested on the development of experimental PH.

Figure 5:
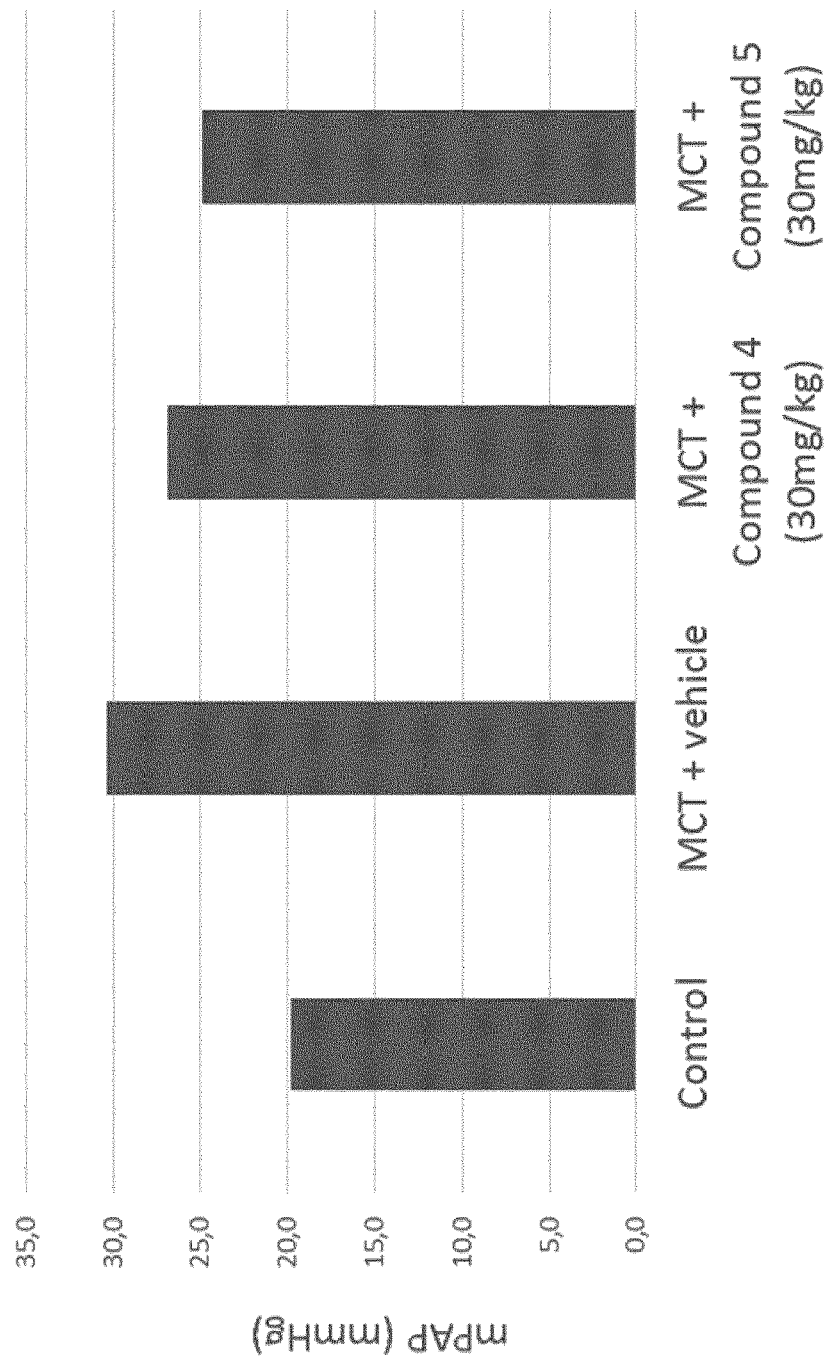
FIG. 5 is a histogram showing the effect of compounds 4 and 5 of the invention on the mean pulmonary arterial pressure (mPAP) of a rat model of PH.

Oral daily treatment for 2 weeks with compound 4 or 5, started one week after a subcutaneous MCT injection substantially attenuates the degree of established PH (FIG. 5). On day 21, in MCT-injected rats treated with vehicle B, a marked increase in mean pulmonary arterial pressure (mPAP), right ventricular hypertrophy (RVH) and numbers of muscularized distal pulmonary arteries were found compared with controls (FIG. 5). There was a substantial reduction ($p<0.05$) in values of mPAP between monocrotaline-injected rats treated with either compound 4 or 5 at a dose of 30 mg/kg as compared to monocrotaline-injected rats treated with vehicle B (FIG. 5).

These results further strongly support the use of the compound of the invention for treating pulmonary hypertension.

Example 5: Efficacies of Treatment with Compound 5 of the Invention on the Progression of MCT-Induced Pulmonary Hypertension—Comparison with Sildenafil Efficacy of compound 5 of the invention (at 30 mg/kg) was tested on the development of experimental PH and compared with treatment with sildenafil (at 100 mg/kg). Sildenafil is currently used in the treatment of PAH.

Figure 6:
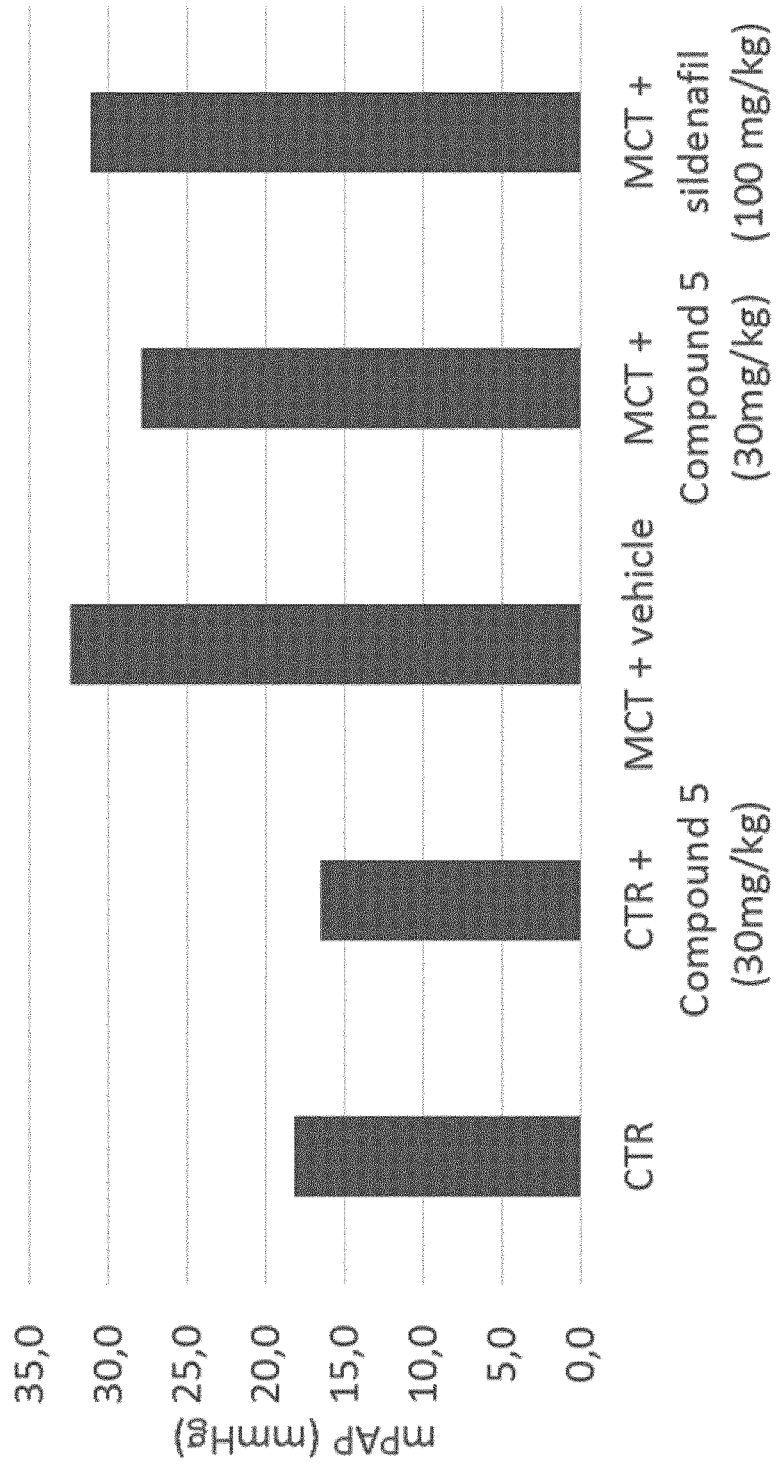
FIG. 6 is a histogram showing the effect of compound 5 of the invention on the mean pulmonary arterial pressure (mPAP) of a rat model of PH, compared to sildenafil.

Oral daily treatment for 2 weeks with compound 5 started one week after a subcutaneous MCT injection substantially attenuates the degree of established PH, compared with treatment by sildenafil (FIG. 6).

The invention claimed is:
1. A method of treating pulmonary hypertension in a subject in need thereof, comprising
administering to the subject a therapeutically effective amount of a compound of Formula I, or a pharmaceutically acceptable enantiomer, salt or solvate thereof, wherein said compound of Formula I is:

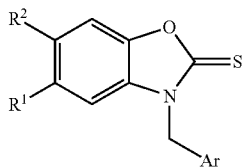

wherein:
Ar represents a substituted or unsubstituted aryl or heteroaryl group; and
$R^1$ and $R^2$ are the same or different and represent a hydrogen atom or a group selected from the group consisting of hydroxyl, amino, halo, nitro, cyano, carboxylic acid, alkyl, cycloalkyl, alkenyl, alkynyl, aryl, heteroaryl, hydroxyalkyl, alkoxy, C1-C8 acyl, and haloalkyl.

2. The method according to claim 1, wherein Formula I is Formula Ia:

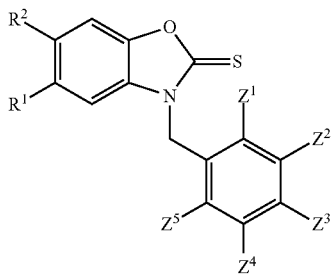

or a pharmaceutically acceptable enantiomer, salt or solvate thereof, wherein:
$R^1$ and $R^2$ are the same or different and represent a hydrogen atom or a group selected from the group consisting of hydroxyl, amino, halo, nitro, cyano, carboxylic acid, alkyl, cycloalkyl, alkenyl, alkynyl, aryl, heteroaryl, hydroxyalkyl, alkoxy, C1-C8 acyl, and haloalkyl;
$Z^1$ represents a hydrogen atom or a group selected from the group consisting of halo, hydroxyl, hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, and 3-hydroxythiophen-2-yl-metanone, or form with $Z^2$ an aryl ring, an heteroaryl ring, a cycloalkyl ring or a heterocyclyl, optionally substituted by one or more groups selected from the group consisting of oxo, halo, hydroxyl, nitro, amino, alkoxy, alkyl, haloalkyl, alkenyl, alkynyl, aryl, and heteroaryl;
$Z^2$ represents a hydrogen atom or a group selected from the group consisting of halo, hydroxyl, hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, and 3-hydroxythiophen-2-yl-metanone, or form with $Z^1$ or $Z^3$ an aryl ring, an heteroaryl ring, a cycloalkyl ring or a heterocyclyl, optionally substituted by one or more groups selected from the group consisting of oxo, halo, hydroxyl, nitro, amino, alkoxy, alkyl, haloalkyl, alkenyl, alkynyl, aryl, and heteroaryl;
$Z^3$ represents a hydrogen atom or a group selected from the group consisting of halo, hydroxyl, hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, and 3-hydroxythiophen-2-yl-metanone, or form with $Z^2$ or $Z^4$ an aryl ring, an heteroaryl ring, a cycloalkyl ring or a heterocyclyl, optionally substituted by one or more groups selected from the group consisting of oxo, halo, hydroxyl, nitro, amino, alkoxy, alkyl, haloalkyl, alkenyl, alkynyl, aryl, and heteroaryl;
$Z^4$ represents a hydrogen atom or a group selected from the group consisting of halo, hydroxyl, hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, and 3-hydroxythiophen-2-yl-metanone, or form with $Z^3$ or $Z^5$ an aryl ring, an heteroaryl ring, a cycloalkyl ring or a heterocyclyl, optionally substituted by one or more groups selected from the group consisting of oxo, halo, hydroxyl, nitro, amino, alkoxy, alkyl, haloalkyl, alkenyl, alkynyl, aryl, and heteroaryl; and
$Z^5$ represents a hydrogen atom or a group selected from the group consisting of halo, hydroxyl, hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, 3-hydroxythiophen-2-yl-metanone, or form with $Z^4$ an aryl ring, an heteroaryl ring, a cycloalkyl ring or a heterocyclyl, optionally substituted by one or more groups selected from the group consisting of oxo, halo, hydroxyl, nitro, amino, alkoxy, alkyl, haloalkyl, alkenyl, alkynyl, aryl, and heteroaryl.

3. The method according to claim 1, wherein Formula I is Formula Ib:

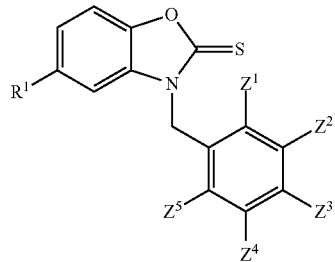

or a pharmaceutically acceptable enantiomer, salt or solvate thereof, wherein
$R^1$ and $R^2$ are the same or different and represent a hydrogen atom or a group selected from the group consisting of hydroxyl, amino, halo, nitro, cyano, carboxylic acid, alkyl, cycloalkyl, alkenyl, alkynyl, aryl, heteroaryl, hydroxyalkyl, alkoxy, C1-C8 acyl, and haloalkyl; and $Z^1$, $Z^2$, Z3, $Z^4$ and $Z^5$ independently represent a hydrogen atom or a group selected from the group consisting of halo, hydroxyl, hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, and 3-hydroxythiophen-2-yl-metanone, or form with $Z^2$ an aryl ring, an heteroaryl ring, a cycloalkyl ring or a heterocyclyl, optionally substituted by one or more groups selected from the group consisting of oxo, halo, hydroxyl, nitro, amino, alkoxy, alkyl, haloalkyl, alkenyl, alkynyl, aryl, and heteroaryl.

4. The method of claim 1, wherein the compound of Formula I is selected from the group consisting of:
   3-(3-hydroxybenzyl)-5-methylbenzo[d]oxazole-2(3H)-thione,
   3-(2-methoxybenzyl)-5-methylbenzo[d]oxazole-2(3H)-thione,
   3-benzyl-5-methylbenzo[d]oxazole-2(3H)-thione,
   3-(4-fluoro-3-hydroxybenzyl)-5-methylbenzo[d]oxazole-2(3H)-thione, and
   3-(4-fluoro-3-hydroxybenzyl)-5-(trifluoromethyl)benzo[d]oxazole-2(3H)-thione.

5. The method of claim 1, wherein the subject is diagnosed with pulmonary hypertension.

6. The method of claim 1, wherein the subject is at risk of developing pulmonary hypertension.

7. The method of claim 1, wherein said subject is an adult, a teenager, a child, a young child or a new born child.

8. The method of claim 1, wherein the step of administering is performed by topical, subcutaneous, oral, transdermal, nasal, parenteral, or intratracheal administration.

9. The method of claim 1, wherein the method is used for acute treatment of pulmonary hypertension.

10. The method of claim 1, wherein the method is used for chronic treatment of pulmonary hypertension.

11. The method of claim 1, wherein the pulmonary hypertension is selected from Groups 1, 1', 1", 2, 3, 4 and 5.

12. The method of claim 1, wherein the pulmonary hypertension is pulmonary arterial hypertension (PAH).

13. The method of claim 12 wherein the pulmonary arterial hypertension is selected from the group consisting of idiopathic PAH, heritable PAH, drug- and toxin-induced PAH, PAH associated with connective tissue diseases, PAH complication of HIV infection, portal hypertension; PAH associated with congenital heart diseases (CHD); and PAH associated with schistosomiasis.

14. The method of claim 1, wherein the substituted or unsubstituted aryl or heteroaryl group is selected from the group consisting of phenyl, pyridine, indole, indazole, 7-azaindole, quinoline, quinolinone, dihydroquinolinone, dihydroquinaolinone, imidazole, pyrrole, or pyrazol, benzimidazolone, benzoxazolone, benzimidazole-thione, benzotriazole, benimidazole, benzoxazinone, indolinedione, hydroxypyridinone, and benzothiazolamine.

15. The method of claim 14, wherein the substituted or unsubstituted aryl or heteroaryl group is substituted by one or more substituents selected from the group consisting of halo, hydroxyl, hydroxyalkyl, nitro, amino, amido, aminoacid, carbamate, carbamide, carbonate, ester, thioester, phosphonate, phosphonate methyloxy, phosphonate methylamino, sulfonamide, alkoxy, alkylthio, alkyl, haloalkyl, alkenyl, alkynyl, aryl, heteroaryl, 4-amino-cyclobut-3-ene-1,2-dione, 3-hydroxythiophen-2-yl-metanone.

16. The method of claim 1, wherein Ar is substituted or unsubstituted phenyl.

17. The method of claim 1, wherein $R^1$ and $R^2$ are the same or different and are hydrogen, alkyl, cycloalkyl or haloalkyl.

18. The method of claim 1, wherein $R^1$ and $R^2$ are the same or different and are hydrogen, methyl or $CF_3$.

19. The method of claim 2, wherein one or more of $Z^1$, $Z^2$, $Z^3$, $Z^{24}$ and $Z^5$ are H, F, Cl, Br, $NO_2$, $NH_2$, $NMe_2$, OH, OMe, $CH_3$ or $CF_3$.

* * * * *